United States Patent
Gopinath et al.

(10) Patent No.: US 11,287,961 B2
(45) Date of Patent: Mar. 29, 2022

(54) INTRAVASCULAR DATA VISUALIZATION AND INTERFACE SYSTEMS AND METHODS

(71) Applicant: LightLab Imaging, Inc., Westford, MA (US)

(72) Inventors: Ajay Gopinath, Bedford, MA (US); Denis Dion, Dracut, MA (US); Christopher E. Griffin, Wilton, NH (US); Desmond Adler, Bedford, MA (US)

(73) Assignee: LightLab Imaging, Inc., Westford, MA (US)

( * ) Notice: Subject to any disclaimer, the term of this patent is extended or adjusted under 35 U.S.C. 154(b) by 0 days.

(21) Appl. No.: 16/444,319

(22) Filed: Jun. 18, 2019

(65) Prior Publication Data
US 2020/0142575 A1 May 7, 2020

Related U.S. Application Data

(63) Continuation of application No. 15/219,197, filed on Jul. 25, 2016, now Pat. No. 10,338,795.
(Continued)

(51) Int. Cl.
*G06F 3/048* (2013.01)
*G06F 3/04847* (2022.01)
(Continued)

(52) U.S. Cl.
CPC ........ *G06F 3/04847* (2013.01); *A61B 5/0066* (2013.01); *A61B 5/0084* (2013.01);
(Continued)

(58) Field of Classification Search
None
See application file for complete search history.

(56) References Cited

U.S. PATENT DOCUMENTS

| 4,548,473 A | 10/1985 | Lo et al. |
| 5,054,492 A | 10/1991 | Scribner et al. |

(Continued)

FOREIGN PATENT DOCUMENTS

| CA | 2887360 A1 | 4/2014 |
| CN | 101264014 A | 9/2008 |

(Continued)

OTHER PUBLICATIONS

Bonnema et al., "An automatic algorithm for detecting stent endothelialization from volumetric optical coherence tomography datasets", Physics in Medicine and Biology, 53 :12, Jun. 21, 2008, pp. 3083-3098.
(Continued)

*Primary Examiner* — Hua Lu
(74) *Attorney, Agent, or Firm* — Lerner, David, Littenberg, Krumholz & Mentlik, LLP

(57) ABSTRACT

In part, the disclosure relates to intravascular data collection systems and the software-based visualization and display of intravascular data relating to detected side branches and detected stent struts. Levels of stent malapposition can be defined using a user interface such as a slider, toggle, button, field, or other interface to specify how indicia are displayed relative to detected stent struts. In addition, the disclosure relates to methods to automatically provide a two or three-dimensional visualization suitable for assessing side branch and/or guide wire location during stenting. The method can use one or more a computed side branch location, a branch takeoff angle, one or more stent strut locations, and one or more lumen contours.

11 Claims, 24 Drawing Sheets

Related U.S. Application Data

(60) Provisional application No. 62/196,997, filed on Jul. 25, 2015.

(51) Int. Cl.
| | | |
|---|---|---|
| *A61B 34/10* | (2016.01) | |
| *A61B 5/00* | (2006.01) | |
| *A61B 34/20* | (2016.01) | |
| *A61B 8/12* | (2006.01) | |
| *G06T 15/08* | (2011.01) | |
| *G06T 7/00* | (2017.01) | |
| *G06T 19/00* | (2011.01) | |
| *G06F 3/04815* | (2022.01) | |
| *A61B 5/02* | (2006.01) | |
| *G16H 30/40* | (2018.01) | |
| *G16H 50/20* | (2018.01) | |
| *G16H 20/40* | (2018.01) | |

(52) U.S. Cl.
CPC ........ *A61B 5/02007* (2013.01); *A61B 5/6876* (2013.01); *A61B 5/743* (2013.01); *A61B 5/7435* (2013.01); *A61B 8/12* (2013.01); *A61B 34/10* (2016.02); *A61B 34/20* (2016.02); *G06F 3/04815* (2013.01); *G06T 7/0012* (2013.01); *G06T 15/08* (2013.01); *G06T 19/003* (2013.01); *G16H 20/40* (2018.01); *G16H 30/40* (2018.01); *G16H 50/20* (2018.01); *A61B 5/6852* (2013.01); *A61B 2034/105* (2016.02); *A61B 2034/2055* (2016.02); *A61B 2034/2063* (2016.02); *G06T 2200/24* (2013.01)

(56) References Cited

U.S. PATENT DOCUMENTS

| | | | |
|---|---|---|---|
| 5,321,501 A | 6/1994 | Swanson et al. | |
| 5,459,570 A | 10/1995 | Swanson et al. | |
| 5,465,147 A | 11/1995 | Swanson | |
| 5,477,858 A | 12/1995 | Norris et al. | |
| 5,488,674 A | 1/1996 | Burt et al. | |
| 5,509,093 A | 4/1996 | Miller et al. | |
| 5,518,810 A | 5/1996 | Nishihara et al. | |
| 5,531,227 A | 7/1996 | Schneider | |
| 5,586,201 A | 12/1996 | Whiting et al. | |
| 5,619,368 A | 4/1997 | Swanson | |
| 5,632,767 A | 5/1997 | Sinofsky | |
| 5,643,253 A | 7/1997 | Baxter et al. | |
| 5,662,109 A | 9/1997 | Hutson | |
| 5,715,827 A | 2/1998 | Corl et al. | |
| 5,748,598 A | 5/1998 | Swanson et al. | |
| 5,771,895 A | 6/1998 | Stager | |
| 5,784,352 A | 7/1998 | Swanson et al. | |
| 5,797,849 A | 8/1998 | Vesely et al. | |
| 5,822,391 A | 10/1998 | Whitting | |
| 5,908,415 A | 6/1999 | Sinofsky | |
| 5,921,931 A * | 7/1999 | O'Donnell ........ G01S 15/8979 | |
| | | | 600/441 |
| 5,947,959 A | 9/1999 | Sinofsky | |
| 5,956,355 A | 9/1999 | Swanson et al. | |
| 5,965,355 A | 10/1999 | Swanson et al. | |
| 5,989,189 A | 11/1999 | LeBlanc et al. | |
| 6,111,645 A | 8/2000 | Tearney et al. | |
| 6,134,003 A | 10/2000 | Tearney et al. | |
| 6,148,095 A | 11/2000 | Prause et al. | |
| 6,160,826 A | 12/2000 | Swanson et al. | |
| 6,191,862 B1 | 2/2001 | Swanson et al. | |
| 6,195,445 B1 | 2/2001 | Jolly et al. | |
| 6,208,883 B1 | 3/2001 | Holupka et al. | |
| 6,270,492 B1 | 8/2001 | Sinofsky | |
| 6,282,011 B1 | 8/2001 | Tearney et al. | |
| 6,302,875 B1 | 10/2001 | Makower et al. | |
| 6,348,960 B1 | 2/2002 | Etori et al. | |
| 6,381,350 B1 | 4/2002 | Klingensmith et al. | |
| 6,385,332 B1 | 5/2002 | Zahalka et al. | |
| 6,421,164 B2 | 7/2002 | Tearney et al. | |
| 6,445,939 B1 * | 9/2002 | Swanson ............ A61B 5/0066 | |
| | | | 385/33 |
| 6,471,656 B1 | 10/2002 | Shalman et al. | |
| 6,485,413 B1 * | 11/2002 | Boppart ............ A61B 1/00096 | |
| | | | 356/450 |
| 6,501,551 B1 * | 12/2002 | Tearney ............ A61B 1/00096 | |
| | | | 356/477 |
| 6,552,796 B2 | 4/2003 | Magnin et al. | |
| 6,564,087 B1 * | 5/2003 | Pitris ............... A61B 1/00172 | |
| | | | 600/478 |
| 6,565,514 B2 | 5/2003 | Svanerudh et al. | |
| 6,570,659 B2 | 5/2003 | Schmitt | |
| 6,585,660 B2 | 7/2003 | Dorando et al. | |
| 6,692,824 B2 | 2/2004 | Benz et al. | |
| 6,697,667 B1 | 2/2004 | Lee et al. | |
| 6,706,004 B2 | 3/2004 | Tearney et al. | |
| 6,716,178 B1 | 4/2004 | Kilpatrick et al. | |
| 6,718,089 B2 | 4/2004 | James et al. | |
| 6,728,566 B1 | 4/2004 | Subramanyan et al. | |
| 6,731,973 B2 | 5/2004 | Voith | |
| 6,760,112 B2 | 7/2004 | Reed et al. | |
| 6,785,409 B1 | 8/2004 | Suri | |
| 6,868,736 B2 | 3/2005 | Sawatari et al. | |
| 6,879,851 B2 | 4/2005 | McNamara et al. | |
| 6,891,984 B2 | 5/2005 | Petersen et al. | |
| 6,932,809 B2 | 8/2005 | Sinofsky | |
| 6,937,696 B1 | 8/2005 | Mostafavi | |
| 6,942,657 B2 | 9/2005 | Sinofsky et al. | |
| 6,947,040 B2 | 9/2005 | Tek et al. | |
| 6,973,202 B2 | 12/2005 | Mostafavi | |
| 6,974,557 B1 | 12/2005 | Webler et al. | |
| 7,048,716 B1 * | 5/2006 | Kucharczyk ...... A61M 25/0043 | |
| | | | 600/411 |
| 7,068,831 B2 | 6/2006 | Florent et al. | |
| 7,134,994 B2 | 11/2006 | Alpert et al. | |
| 7,191,100 B2 | 3/2007 | Mostafavi | |
| 7,208,333 B2 | 4/2007 | Flanders et al. | |
| 7,231,243 B2 * | 6/2007 | Tearney ............ A61B 1/00082 | |
| | | | 600/407 |
| 7,241,286 B2 | 7/2007 | Atlas | |
| 7,298,478 B2 | 11/2007 | Gilbert et al. | |
| 7,301,644 B2 | 11/2007 | Knighton et al. | |
| 7,321,677 B2 | 1/2008 | Evron et al. | |
| 7,329,223 B1 | 2/2008 | Ainsworth et al. | |
| 7,355,699 B2 | 4/2008 | Gilbert et al. | |
| 7,359,554 B2 | 4/2008 | Klingensmith et al. | |
| 7,397,935 B2 | 7/2008 | Kimmel et al. | |
| 7,408,648 B2 | 8/2008 | Kleen et al. | |
| 7,412,141 B2 | 8/2008 | Gowda et al. | |
| 7,414,779 B2 | 8/2008 | Huber et al. | |
| 7,415,049 B2 | 8/2008 | Flanders et al. | |
| 7,450,241 B2 | 11/2008 | Zuluaga | |
| RE40,608 E | 12/2008 | Glover et al. | |
| 7,492,522 B2 | 2/2009 | Gilbert et al. | |
| 7,532,920 B1 | 5/2009 | Ainsworth et al. | |
| 7,576,861 B2 | 8/2009 | Gilbert et al. | |
| 7,593,559 B2 | 9/2009 | Toth et al. | |
| 7,610,081 B2 | 10/2009 | Redel | |
| 7,619,646 B2 | 11/2009 | Freifeld et al. | |
| 7,625,366 B2 | 12/2009 | Atlas | |
| 7,627,156 B2 | 12/2009 | Margolis et al. | |
| 7,650,179 B2 | 1/2010 | Redel et al. | |
| 7,679,754 B2 | 3/2010 | Zuluaga | |
| 7,697,972 B2 | 4/2010 | Verard et al. | |
| 7,706,585 B2 | 4/2010 | Kleen | |
| 7,711,413 B2 | 5/2010 | Feldman et al. | |
| 7,729,746 B2 | 6/2010 | Redel et al. | |
| 7,733,497 B2 | 6/2010 | Yun et al. | |
| 7,742,797 B2 | 6/2010 | Redel et al. | |
| 7,783,337 B2 | 8/2010 | Feldman et al. | |
| 7,783,338 B2 | 8/2010 | Ainsworth et al. | |
| 7,785,286 B2 | 8/2010 | Magnin et al. | |
| 7,792,342 B2 | 9/2010 | Barbu et al. | |
| 7,801,343 B2 | 9/2010 | Unal et al. | |
| 7,813,609 B2 | 10/2010 | Petersen et al. | |
| 7,831,078 B2 | 11/2010 | Unal et al. | |
| 7,843,976 B2 | 11/2010 | Cable et al. | |

(56) References Cited

U.S. PATENT DOCUMENTS

| | | | |
|---|---|---|---|
| 7,848,791 B2 | 12/2010 | Schmitt et al. | |
| 7,853,316 B2 | 12/2010 | Milner et al. | |
| 7,869,663 B2 | 1/2011 | Buckland et al. | |
| 7,872,759 B2 | 1/2011 | Tearney et al. | |
| 7,916,387 B2 | 3/2011 | Schmitt | |
| 7,918,793 B2 | 4/2011 | Altmann et al. | |
| 7,925,327 B2 | 4/2011 | Weese | |
| 7,930,014 B2 | 4/2011 | Huennekens et al. | |
| 7,935,060 B2 | 5/2011 | Schmitt et al. | |
| 7,967,743 B2 | 6/2011 | Ishihara | |
| 7,988,633 B2 | 8/2011 | Hossack et al. | |
| 7,991,105 B2 | 8/2011 | Mielekamp et al. | |
| 8,029,447 B2 | 10/2011 | Kanz et al. | |
| 8,116,605 B2 | 2/2012 | Petersen et al. | |
| 8,206,374 B2 | 6/2012 | Duane et al. | |
| 8,206,377 B2 * | 6/2012 | Petroff | F16D 9/06 604/535 |
| 8,208,995 B2 | 6/2012 | Tearney et al. | |
| 8,223,143 B2 | 7/2012 | Dastmalchi et al. | |
| 8,259,303 B2 | 9/2012 | Johnson et al. | |
| 8,290,228 B2 | 10/2012 | Cohen et al. | |
| 8,298,147 B2 | 10/2012 | Huennekens et al. | |
| 8,315,282 B2 | 11/2012 | Huber et al. | |
| 8,325,419 B2 | 12/2012 | Schmitt | |
| 8,351,665 B2 | 1/2013 | Tearney et al. | |
| 8,358,461 B2 | 1/2013 | Huber et al. | |
| 8,412,312 B2 | 4/2013 | Judell et al. | |
| 8,423,121 B2 | 4/2013 | Wang et al. | |
| 8,449,468 B2 | 5/2013 | Petersen et al. | |
| 8,457,375 B2 | 6/2013 | Rieber et al. | |
| 8,457,440 B1 | 6/2013 | Johnson | |
| 8,463,007 B2 | 6/2013 | Steinberg et al. | |
| 8,478,384 B2 | 7/2013 | Schmitt et al. | |
| 8,478,387 B2 | 7/2013 | Xu | |
| 8,503,844 B2 | 8/2013 | Petersen et al. | |
| 8,542,900 B2 | 9/2013 | Tolkowsky et al. | |
| 8,556,820 B2 | 10/2013 | Alpert et al. | |
| 8,562,537 B2 | 10/2013 | Alpert et al. | |
| 8,571,639 B2 | 10/2013 | Mostafavi | |
| 8,581,643 B1 | 11/2013 | Schmitt | |
| 8,582,109 B1 | 11/2013 | Schmitt | |
| 8,582,619 B2 | 11/2013 | Adler | |
| 8,582,934 B2 | 11/2013 | Adler et al. | |
| 8,670,603 B2 | 3/2014 | Tolkowsky et al. | |
| 8,687,201 B2 | 4/2014 | Adler | |
| 8,693,756 B2 | 4/2014 | Tolkowsky et al. | |
| 8,700,130 B2 | 4/2014 | Iddan et al. | |
| 8,781,193 B2 | 7/2014 | Steinberg et al. | |
| 8,786,336 B1 | 7/2014 | Schmitt | |
| 8,831,321 B1 | 9/2014 | Elbasiony | |
| 8,855,744 B2 | 10/2014 | Tolkowsky et al. | |
| 8,909,323 B2 | 12/2014 | Baumgart | |
| 8,913,084 B2 | 12/2014 | Chen et al. | |
| 8,948,228 B2 | 2/2015 | Adler | |
| 8,953,911 B1 | 2/2015 | Xu et al. | |
| 8,983,580 B2 | 3/2015 | Boppart et al. | |
| 9,069,396 B2 | 6/2015 | Adler et al. | |
| 9,173,591 B2 | 11/2015 | Elbasiony et al. | |
| 9,308,052 B2 | 4/2016 | Tolkowsky et al. | |
| 9,351,698 B2 | 5/2016 | Dascal et al. | |
| 9,404,731 B2 | 8/2016 | Adler et al. | |
| 9,435,956 B1 | 9/2016 | Xu et al. | |
| 9,488,464 B1 | 11/2016 | Schmitt | |
| 9,629,571 B2 | 4/2017 | Tolkowsky et al. | |
| 2002/0115931 A1 | 8/2002 | Strauss et al. | |
| 2002/0161351 A1 | 10/2002 | Samson et al. | |
| 2004/0006277 A1 | 1/2004 | Langenhove et al. | |
| 2005/0043614 A1 | 2/2005 | Huizenga et al. | |
| 2005/0049672 A1 * | 3/2005 | Murphy | A61B 17/12022 623/1.12 |
| 2005/0201662 A1 * | 9/2005 | Petersen | G02B 23/2407 385/12 |
| 2005/0238067 A1 | 10/2005 | Choi | |
| 2005/0249391 A1 | 11/2005 | Kimmel et al. | |
| 2006/0095065 A1 | 5/2006 | Tanimura et al. | |
| 2006/0135870 A1 | 6/2006 | Webler | |
| 2006/0165270 A1 | 7/2006 | Borgert et al. | |
| 2006/0187537 A1 | 8/2006 | Huber et al. | |
| 2006/0203859 A1 | 9/2006 | Cable et al. | |
| 2006/0241465 A1 | 10/2006 | Huennekens et al. | |
| 2006/0241503 A1 | 10/2006 | Schmitt et al. | |
| 2006/0244973 A1 | 11/2006 | Yun et al. | |
| 2007/0024617 A1 | 2/2007 | Poole | |
| 2007/0055132 A1 | 3/2007 | Camus et al. | |
| 2007/0060822 A1 | 3/2007 | Alpert et al. | |
| 2007/0066890 A1 | 3/2007 | Maschke | |
| 2007/0115481 A1 | 5/2007 | Toth et al. | |
| 2007/0123771 A1 | 5/2007 | Redel et al. | |
| 2007/0135803 A1 | 6/2007 | Belson | |
| 2007/0165916 A1 | 7/2007 | Cloutier et al. | |
| 2007/0167710 A1 * | 7/2007 | Unal | A61B 5/0066 600/407 |
| 2007/0232933 A1 | 10/2007 | Gille et al. | |
| 2007/0260198 A1 | 11/2007 | Atlas | |
| 2007/0293932 A1 | 12/2007 | Zilla et al. | |
| 2008/0100612 A1 | 5/2008 | Dastmalchi et al. | |
| 2008/0161696 A1 | 7/2008 | Schmitt et al. | |
| 2008/0165366 A1 | 7/2008 | Schmitt | |
| 2008/0177139 A1 * | 7/2008 | Courtney | A61B 5/742 600/109 |
| 2008/0221439 A1 * | 9/2008 | Iddan | A61B 5/02007 600/424 |
| 2008/0221440 A1 | 9/2008 | Iddan et al. | |
| 2008/0221442 A1 | 9/2008 | Tolkowsky et al. | |
| 2008/0228086 A1 | 9/2008 | Ilegbusi et al. | |
| 2008/0281205 A1 * | 11/2008 | Naghavi | A61B 8/12 600/458 |
| 2009/0027051 A1 | 1/2009 | Stuber et al. | |
| 2009/0174931 A1 | 7/2009 | Huber et al. | |
| 2009/0204134 A1 | 8/2009 | Kassab | |
| 2009/0264768 A1 * | 10/2009 | Courtney | A61B 5/0066 600/463 |
| 2009/0306520 A1 * | 12/2009 | Schmitt | A61B 5/6852 600/476 |
| 2010/0076320 A1 | 3/2010 | Petersen et al. | |
| 2010/0094127 A1 * | 4/2010 | Xu | A61B 5/7425 600/425 |
| 2010/0142785 A1 * | 6/2010 | Dahnke | G01R 33/286 382/131 |
| 2010/0157041 A1 | 6/2010 | Klaiman et al. | |
| 2010/0160764 A1 | 6/2010 | Steinberg et al. | |
| 2010/0160773 A1 | 6/2010 | Cohen et al. | |
| 2010/0161023 A1 | 6/2010 | Cohen et al. | |
| 2010/0172556 A1 | 7/2010 | Cohen et al. | |
| 2010/0191102 A1 | 7/2010 | Steinberg et al. | |
| 2010/0222671 A1 | 9/2010 | Cohen et al. | |
| 2010/0228076 A1 | 9/2010 | Blank | |
| 2010/0232672 A1 | 9/2010 | Jandt et al. | |
| 2010/0253949 A1 | 10/2010 | Adler et al. | |
| 2011/0007315 A1 | 1/2011 | Petersen et al. | |
| 2011/0034814 A1 | 2/2011 | Kopperschmidt | |
| 2011/0071404 A1 * | 3/2011 | Schmitt | A61B 5/0066 600/479 |
| 2011/0071405 A1 | 3/2011 | Judell et al. | |
| 2011/0101207 A1 | 5/2011 | Schmitt | |
| 2011/0151980 A1 | 6/2011 | Petroff | |
| 2011/0157686 A1 | 6/2011 | Huber et al. | |
| 2011/0172511 A1 | 7/2011 | Schmitt et al. | |
| 2011/0178413 A1 | 7/2011 | Schmitt et al. | |
| 2011/0190586 A1 * | 8/2011 | Kemp | A61B 1/12 600/156 |
| 2011/0216325 A1 | 9/2011 | Schmitt | |
| 2011/0228280 A1 | 9/2011 | Schmitt et al. | |
| 2011/0230758 A1 | 9/2011 | Eichler | |
| 2011/0257545 A1 | 10/2011 | Suri | |
| 2011/0263960 A1 * | 10/2011 | Mitchell | A61F 2/958 600/373 |
| 2011/0319752 A1 | 12/2011 | Steinberg et al. | |
| 2012/0004529 A1 | 1/2012 | Tolkowsky et al. | |
| 2012/0029339 A1 | 2/2012 | Cohen et al. | |
| 2012/0057157 A1 | 3/2012 | Petersen et al. | |
| 2012/0075638 A1 * | 3/2012 | Rollins | A61B 1/00009 356/479 |

(56) References Cited

U.S. PATENT DOCUMENTS

| | | |
|---|---|---|
| 2012/0130243 A1 | 5/2012 | Balocco et al. |
| 2012/0162660 A1 | 6/2012 | Kemp |
| 2012/0224751 A1 | 9/2012 | Kemp et al. |
| 2012/0236883 A1 | 9/2012 | Adler |
| 2012/0238869 A1 | 9/2012 | Schmitt et al. |
| 2012/0250028 A1 | 10/2012 | Schmitt et al. |
| 2012/0300215 A1 | 11/2012 | Johnson et al. |
| 2012/0300216 A1 | 11/2012 | Johnson et al. |
| 2012/0310081 A1 | 12/2012 | Adler et al. |
| 2012/0316433 A1 | 12/2012 | Maruyama |
| 2012/0316491 A1* | 12/2012 | Jonsson ............ A61B 17/12136 604/26 |
| 2012/0323311 A1* | 12/2012 | McClain ................ A61L 31/16 623/1.42 |
| 2013/0006105 A1 | 1/2013 | Furuichi |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff |
| 2013/0072805 A1 | 3/2013 | Schmitt et al. |
| 2013/0123616 A1 | 5/2013 | Merritt et al. |
| 2013/0303910 A1 | 11/2013 | Hubbard et al. |
| 2013/0310698 A1 | 11/2013 | Judell et al. |
| 2014/0018669 A1 | 1/2014 | Xu |
| 2014/0024931 A1* | 1/2014 | Winston ............... A61B 5/0066 600/427 |
| 2014/0094660 A1 | 4/2014 | Tolkowsky et al. |
| 2014/0094689 A1 | 4/2014 | Cohen et al. |
| 2014/0094691 A1 | 4/2014 | Steinberg et al. |
| 2014/0094692 A1 | 4/2014 | Tolkowsky et al. |
| 2014/0094693 A1 | 4/2014 | Cohen et al. |
| 2014/0094697 A1 | 4/2014 | Petroff et al. |
| 2014/0114182 A1 | 4/2014 | Petersen et al. |
| 2014/0114184 A1 | 4/2014 | Klaiman et al. |
| 2014/0114185 A1 | 4/2014 | Tolkowsky et al. |
| 2014/0142427 A1 | 5/2014 | Petroff |
| 2014/0142432 A1* | 5/2014 | Hutchins .............. A61B 5/0035 600/462 |
| 2014/0142436 A1 | 5/2014 | Hutchins et al. |
| 2014/0146950 A1 | 5/2014 | Chida et al. |
| 2014/0163664 A1* | 6/2014 | Goldsmith ......... A61B 17/0057 623/1.11 |
| 2014/0187929 A1 | 7/2014 | Schmitt et al. |
| 2014/0218742 A1 | 8/2014 | Adler |
| 2014/0249407 A1 | 9/2014 | Adler et al. |
| 2014/0257087 A1 | 9/2014 | Elbasiony et al. |
| 2014/0268167 A1 | 9/2014 | Friedman et al. |
| 2014/0270445 A1 | 9/2014 | Kemp |
| 2014/0276011 A1 | 9/2014 | Schmitt et al. |
| 2014/0276020 A1 | 9/2014 | Hutchins et al. |
| 2014/0286541 A1 | 9/2014 | Kiyomizu et al. |
| 2014/0309536 A1 | 10/2014 | Douk et al. |
| 2014/0316758 A1* | 10/2014 | Yagi ........................ A61B 5/026 703/9 |
| 2014/0379269 A1 | 12/2014 | Schmitt |
| 2015/0119707 A1 | 4/2015 | Schmitt |
| 2015/0153157 A1 | 6/2015 | Schmitt et al. |
| 2015/0190054 A1 | 7/2015 | Kaneko |
| 2015/0192405 A1 | 7/2015 | Schmitt |
| 2015/0297373 A1 | 10/2015 | Schmitt et al. |
| 2015/0370229 A1 | 12/2015 | Adler et al. |
| 2016/0000406 A1 | 1/2016 | Petroff |
| 2016/0022208 A1 | 1/2016 | Gopinath |
| 2016/0058307 A1* | 3/2016 | Svanerudh ............. A61B 5/742 600/427 |
| 2016/0066880 A1* | 3/2016 | Stigall .................. A61B 8/5207 600/424 |
| 2016/0070066 A1 | 3/2016 | Schmitt et al. |
| 2016/0073885 A1 | 3/2016 | Adler |
| 2016/0166232 A1* | 6/2016 | Merritt ..................... A61B 8/12 623/1.11 |
| 2016/0174925 A1 | 6/2016 | Dascal et al. |
| 2016/0292857 A1 | 10/2016 | Begin et al. |
| 2016/0313507 A1 | 10/2016 | Adler et al. |
| 2016/0335763 A1 | 11/2016 | Ambwani et al. |
| 2016/0335766 A1 | 11/2016 | Ambwani et al. |

FOREIGN PATENT DOCUMENTS

| | | |
|---|---|---|
| CN | 101779222 A | 7/2010 |
| CN | 102014984 A | 4/2011 |
| CN | 102046071 A | 5/2011 |
| CN | 102802492 A | 11/2012 |
| CN | 103619256 A | 3/2014 |
| CN | 104063679 A | 9/2014 |
| EP | 1833363 A2 | 9/2007 |
| EP | 2062526 A1 | 5/2009 |
| EP | 2713858 A1 | 4/2014 |
| EP | 3053505 A1 | 8/2016 |
| JP | S63127201 A | 5/1988 |
| JP | 2012505669 A | 3/2012 |
| JP | 2013505782 A | 2/2013 |
| JP | 2013154192 A | 8/2013 |
| JP | 2014158619 A | 9/2014 |
| JP | 2014525761 A | 10/2014 |
| KR | 20140092102 A | 7/2014 |
| WO | 0122870 A1 | 4/2001 |
| WO | 2006076409 A2 | 7/2006 |
| WO | 2007002685 A2 | 1/2007 |
| WO | 2011038044 A2 | 3/2011 |
| WO | 2012126070 A1 | 9/2012 |
| WO | 2012166332 A1 | 12/2012 |
| WO | 2012176191 A1 | 12/2012 |
| WO | 2013049123 A1 | 4/2013 |
| WO | 2013175472 A2 | 11/2013 |
| WO | 2014002095 A2 | 1/2014 |
| WO | 2014045327 A1 | 3/2014 |
| WO | 2014137353 A1 | 9/2014 |
| WO | 2014175853 A1 | 10/2014 |
| WO | 2015044987 A1 | 4/2015 |

OTHER PUBLICATIONS

Briguori et al., "Intravascular ultrasound criteria for the assessment of the functional significance of intermediate coronary artery stenoses and comparison with fractional flow reserve," Am J. Cardiol 87:136-141, 2001.

Chinese Search Report for International Application No. 201680036611.9, dated Mar. 1, 2021, 8 pages.

Dave Fornell, "The Advantages and Disadvantages of OCT vs. IVUS", Diagnostic and Interventional Cardiology, May 18, 2011, pp. 1-4.

Gabriele Alex et al: "Reproducibility of the Carpet View system: a novel technical solution for display and off line analysis of OCT images", International Journal of Cardiovascular Imaging, Kluwer Academic Publishers, Dordrecht, NL, vol. 30, No. 7, Jun. 14, 2014 (Jun. 14, 2014), pp. 1225-1233, XP035393911, ISSN: 1569-5794, DOI: 10.1007/810554-014-0464-2 [retrieved on Jun. 14, 2014].

Gil et al., "Automatic segmentation of artery wall in coronary IVUS images: a probabilistic approach," Computers in Cardiology 2000; 27:687-690.

Haas et al., "Segmentation of 3D intravascular ultrasonic images based on a random field model," Ultrasound in Medicine & Biology, 26:2, 297-306, 2000.

Hariri et al., "An automatic image processing algorithm for initiating and terminating intracoronary OFDI pullback" Biomedical Optics Express 1:2 566-573 (Sep. 1, 2010).

Harrison et al., "The value of lesion cross-sectional area determined by quantitative coronary angiography in assessing the physiologic significance of proximal left anterior descending coronary arterial stenoses," Circulation 69:6 1111-1119, 1984.

Herrington et al., "Semi-automated boundary detection for intravascular ultrasound," Computers in Cardiology 1992 Proceedings., pp. 103-106, Oct. 1992.

International Search Report and Written Opinion for International application No. PCT/US2016/032933 mailed from International Searching Authority dated Aug. 1, 2016 (14 pages).

(56) References Cited

OTHER PUBLICATIONS

International Search Report and Written Opinion of the International Searching Authority for International application No. PCT/US2016/032908, dated Sep. 23, 2016 (13 pages).
Kassab et al., "The pattern of coronary arteriolar bifurcations and the uniform shear hypothesis," Annals of Biomedical Engineering 23 (1): 13-20, 1995.
Kirkeeide, "Coronary obstructions, morphology, and physiological significance," in Reiber JHC and Serruys PW (eds.), Quantitative Coronary Arteriography, Kluwer Academic Publishers, the Netherlands, 1991, pp. 229-244.
Kolyva et al, "Increased diastolic time fraction as beneficial adjunct of a1-adrenergic receptor blockade after percutaneous coronary intervention," Am J Physiol Heart Circ Physiol 295: H2054-H2060, 2008.
Kolyva et al., "'Windkesselness' of coronary arteries hampers assessment of human coronary wave speed by single-point technique," Am J Physiol Heart Circ Physiol, 295: H482-H490, 2008.
Kovalski et al., "Three-dimensional automatic quantitative analysis of intravascular ultrasound images," Ultrasound in Medicine & Biology, 26(4):527-537, 2000.
Laslett, "Normal left main coronary artery diameter can be predicted from diameters of its branch vessels," Clinical Cardiology 18 (10): 580-582, 1995.
Mojsilovic et al., "Automatic segmentation of intravascular ultrasound images: A texture-based approach," Annals of Biomedical Engineering, 25:1059-1071, Nov. 1997.
Ofili et al., "Differential characterization of blood flow, velocity, and vascular resistance between proximal and distal normal epicardial human coronary arteries: analysis by intracoronary Doppler spectral flow velocity," Am Heart J .30:1 37-46, 1995.
Ohta et al, "Rheological Changes After Stenting of a Cerebral Aneurysm: A Finite Element Modeling Approach," Cardiovascular and Interventional Radiology (2005) 28:768-772.
Palti-Wasserman et al., "Identifying and Tracking a Guide Wire in the Coronary Arteries During Angioplasty from X-Ray Images", IEEE transactions on biomedical engineering, 44:2, Feb. 1997, pp. 152-164.
Perez-Rovira et al, "Deformable Registration of Retinal Fluorescein Angiogram Sequences Using Vasculature Structures", 32nd Annual Cont. of IEEE EMBS, 2010, pp. 4383-4386.
Pijls et al., "Fractional Flow Reserve (FFR) Post-Stent Registry Investigators" Coronary pressure measurement after stenting predicts adverse events at follow-up: a multicenter registry, Circulation 2002; 105:2950-2954.
Pujol et al., "Intravascular Ultrasound Images Vessel Characterization using AdaBoost," Functional Imaging and Modeling of the Heart: Lecture Notes in Computer Science, pp. 242-251, 2003.
Seiler et al., "Basic structure-function relations of the epicardial coronary vascular tree, Basis of quantitative coronary arteriography for diffuse coronary artery disease," Circulation 85 (6): 1987-2003, 1992.
Shengxian Tu et al., "In vivo comparison of arterial lumen dimensions assessed by co-registered three-dimensional (3D) quantitative coronary angiography, intravascular ultrasound and optical coherence tomography", Int. J. Cardiovasc Imaging (2012)28:1315-1327.
Siebes et al, "Single-wire pressure and flow velocity measurement to quantify coronary stenosis hemodynamics and effects of percutaneous interventions," Circulation 109:756-762, 2004.
Sihan et al., "A Novel Approach to Quantitative Analysis of Intravascular Optical Coherence Tomography Imaging," Computers in Cardiology 2008; 35:1089-1092.

Sihan et al., "Fully Automatic Three-Dimensional Quantitative Analysis of Intracoronary Optical Coherence Tomography: Method and Validation," Catheterization and Cardiovascular Interventions 74:1058-1065 (2009).
Sonka et al., "Segmentation of intravascular ultrasound images: a knowledge-based approach," IEEE Transactions on Medical Imaging, 14(4):719-732, Dec. 1995.
Span, "Coronary Blood Flow," Ch 12. Dordrecht, The Netherlands: Kluwer Acedemic Publishers, Boston; 1991: pp. 333-361.
Takagi et al., "Clinical potential of intravascular ultrasound for physiological assessment of coronary stenosis," Circulation 100: 250-255, 1999.
Takano et al.. "Evaluation by Optical Coherence Tomography of Neointimal Coverage of Sirolimus-Eiuting Stent Three Months After Implantation," American Journal of Cardiology, vol. 99, No. 8, Apr. 14, 2007, pp. 1033-1038.
Taki et al., "Automatic segmentation of calcified plaques and vessel borders in IVUS images," International Journal of Computer Assisted Radiology and Surgery, 3(3-4):347-354, Sep. 2008.
Tung et al., "Automatic Detection of Coronary Stent Struts in Intravascular OCT Imaging," Proceedings of SPIE, vol. 8315, Feb. 22, 2012 (8 pgs.).
Unai et al., "Stent implant follow-up in intravascular optical coherence tomography images," Int J Cardiovasc Imaging, DOI 10.1007/s10554-009-9508-4, published online Sep. 24, 2009, 8 pgs.
Van den Berg et al., "Using three-dimensional rotational angiography for sizing of covered stents," Am. J. Roentgenology, 178:149-152 (2002).
Verhoeff et al., "Influence of percutaneous coronary intervention on coronary microvascular resistance index," Circulation 111:76-82, 2005.
Wang et al: "Automatic stent strut detection in intravascular optical coherence tomographic pullback runs", Int. J. Cardiovasc Imaging, 2013 (Year: 2013).
Wang, et al., "3D Assessment of Stent Cell Size and Side Branch Access in Intravascular Optical Coherence Tomographic Pullback Runs," Computerized Medical Imaging and Graphics, Mar. 2014, pp. 113-122, vol. 38, No. 2.
White et al., "Does visual interpretation of the coronary angiogram predict the physiologic importance of coronary stenoses?," N Engl J Med 310:13 819-824, 1984.
Wilson et al., "Prediction of the physiologic significance of coronary arterial lesions by quantitative lesion geometry in patients with limited coronary artery disease," Circulation 75: 723-732, 1987.
Wong et al., "A novel method of coronary stent sizing using intravascular ultrasound: safety and clinical outcomes," Int J. Angiol. , 18(1): 22-24 2009.
Xu et al., "Characterization of atherosclerosis plaques by measuring both backscattering and attenuation coefficients in optical coherence tomography," Journal of Biomedical Optics, 13:3, May/Jun. 2008, 8 pgs.
Chinese Search Report for Application No. 201680049576.4, dated Jul. 5, 2021, 7 pages.
Li Y, Gutiérrez-Chico JL, Holm NR, Yang W, Hebsgaard L, Christiansen EH, Maeng M, Lassen JF, Yan F, Reiber JH, Tu S. Impact of side branch modeling on computation of endothelial shear stress in coronary artery disease: coronary tree reconstruction by fusion of 3D angiography and OCT. Journal of the American College of Cardiology. Jul. 14, 2015;66(2):125-35.
Search Report from Third Office Action for Chinese Application No. 201680048506.7 dated Jul. 1, 2021; 3 pages.
Wang et al., Biomedical Optics Express "Fully automated side branch detection in intravascular optical coherence tomography pullback runs" Aug. 2014, pp. 3160-3173, vol. 5 No. 9.

\* cited by examiner

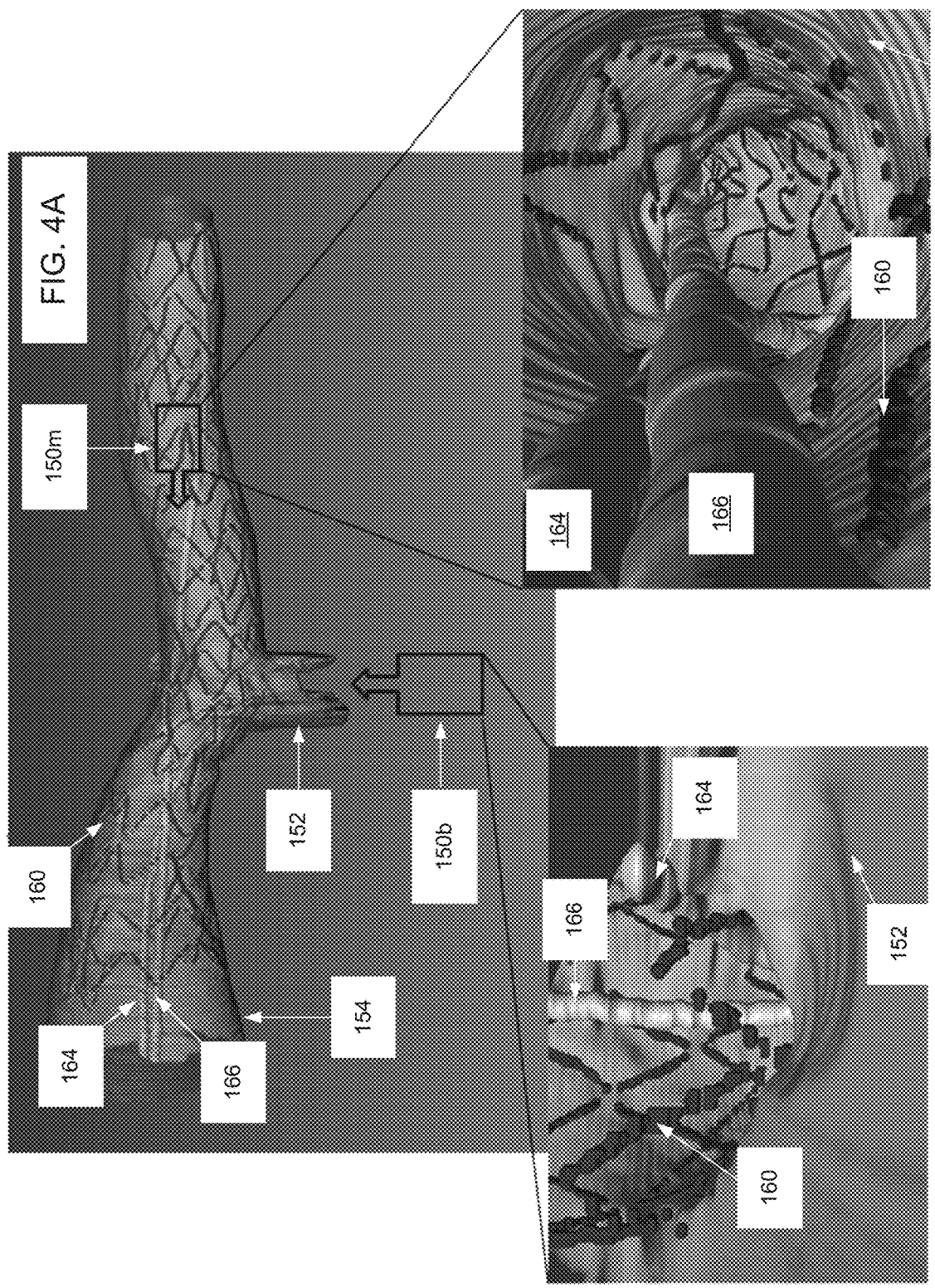

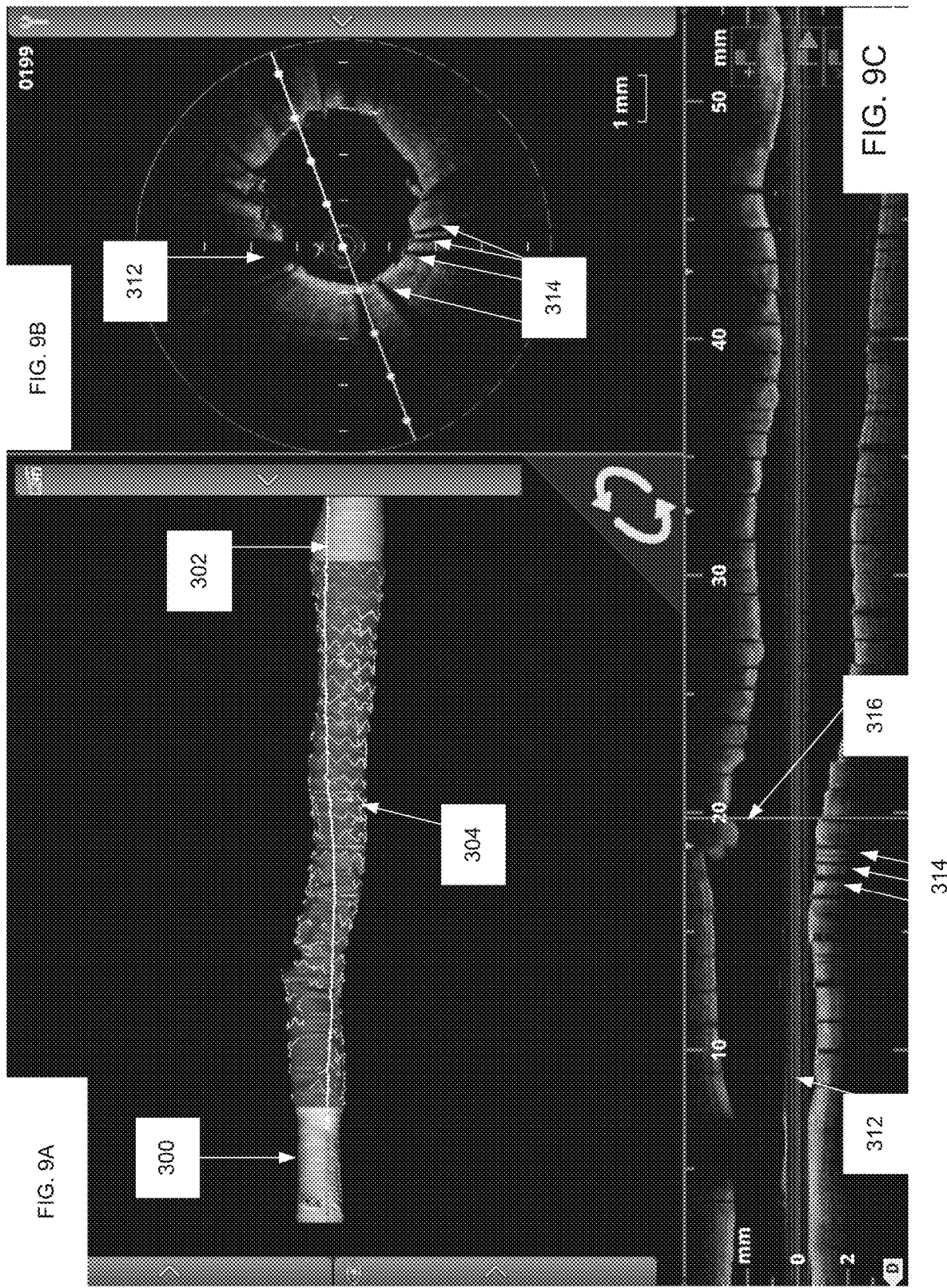

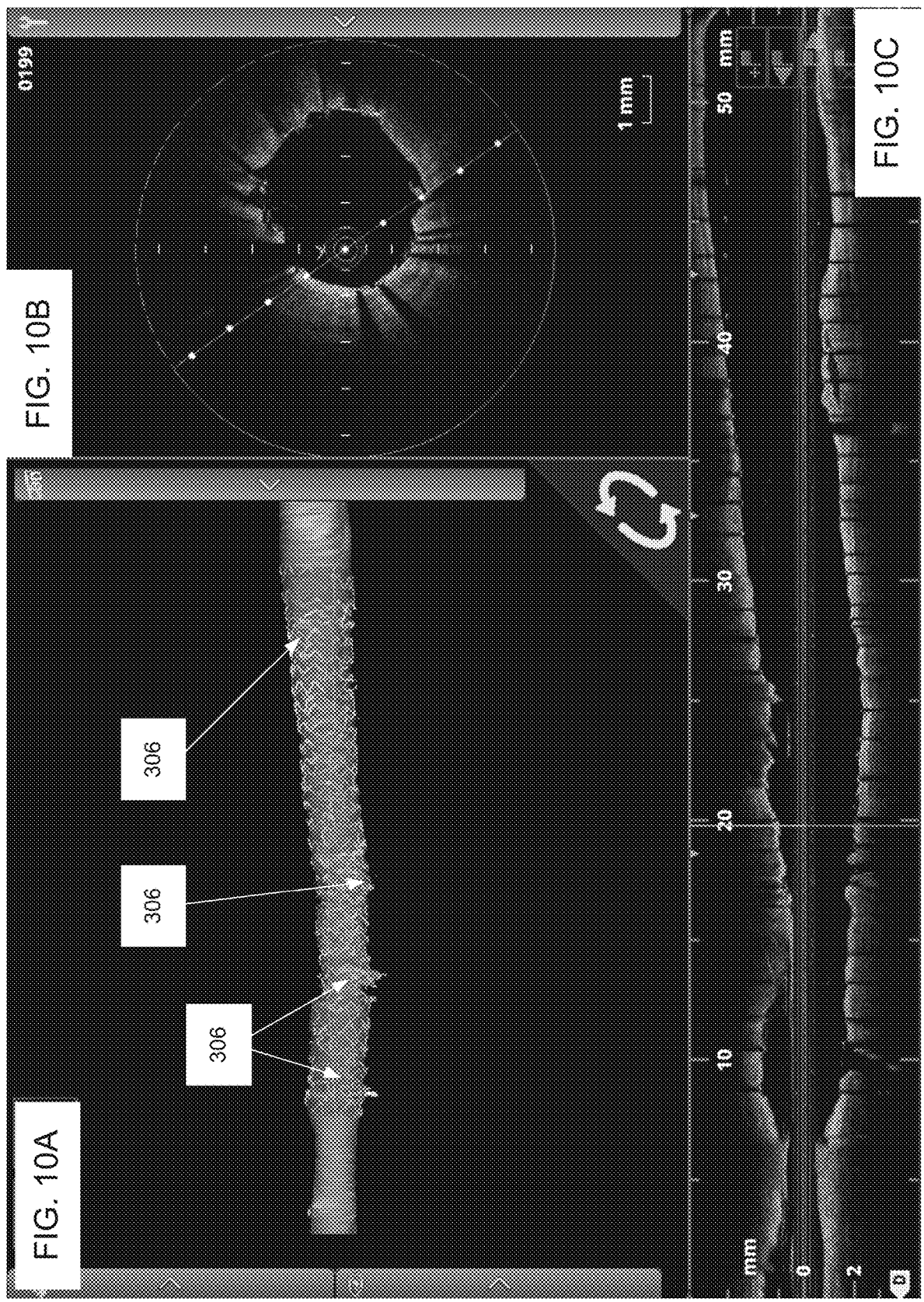

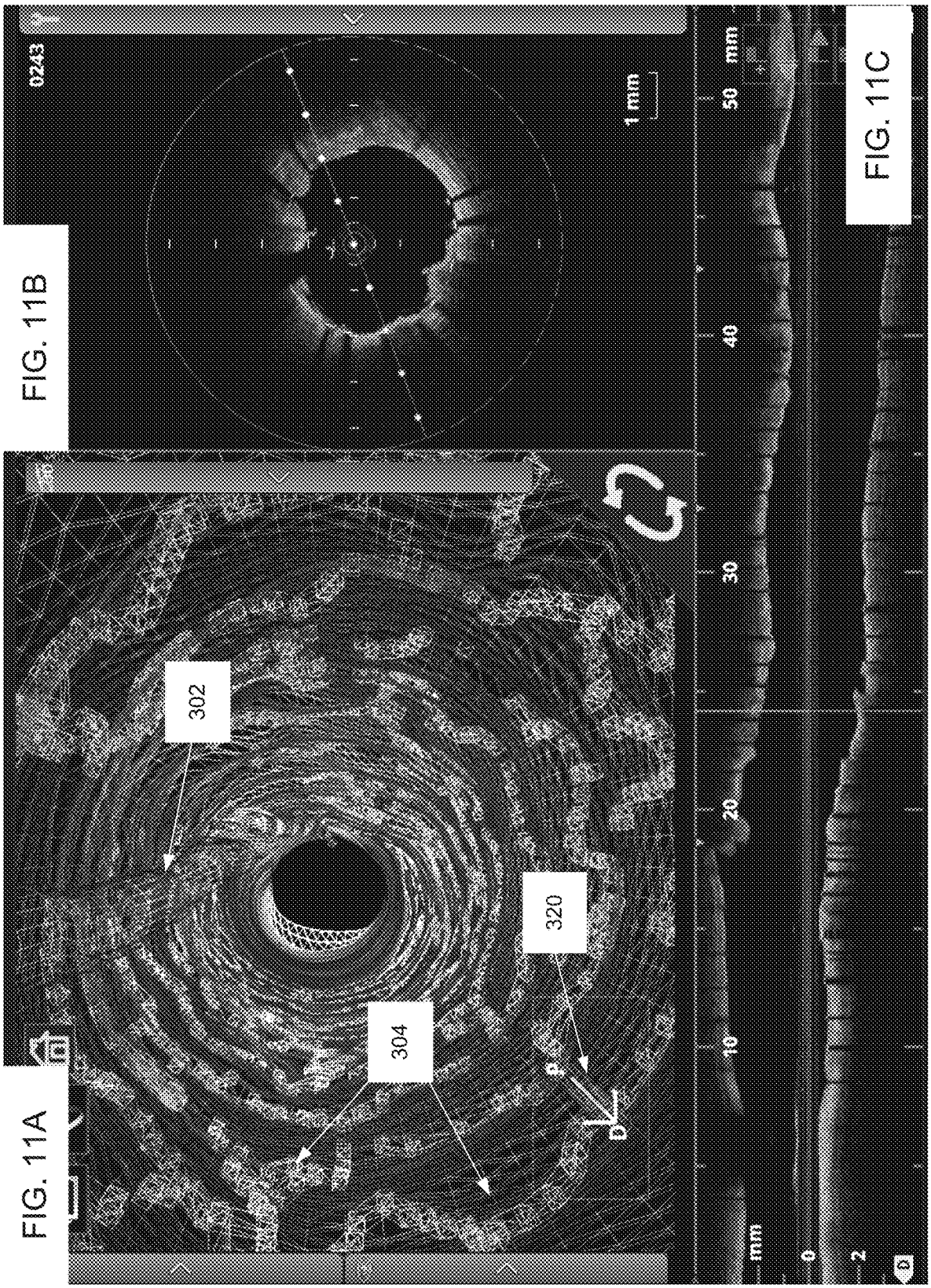

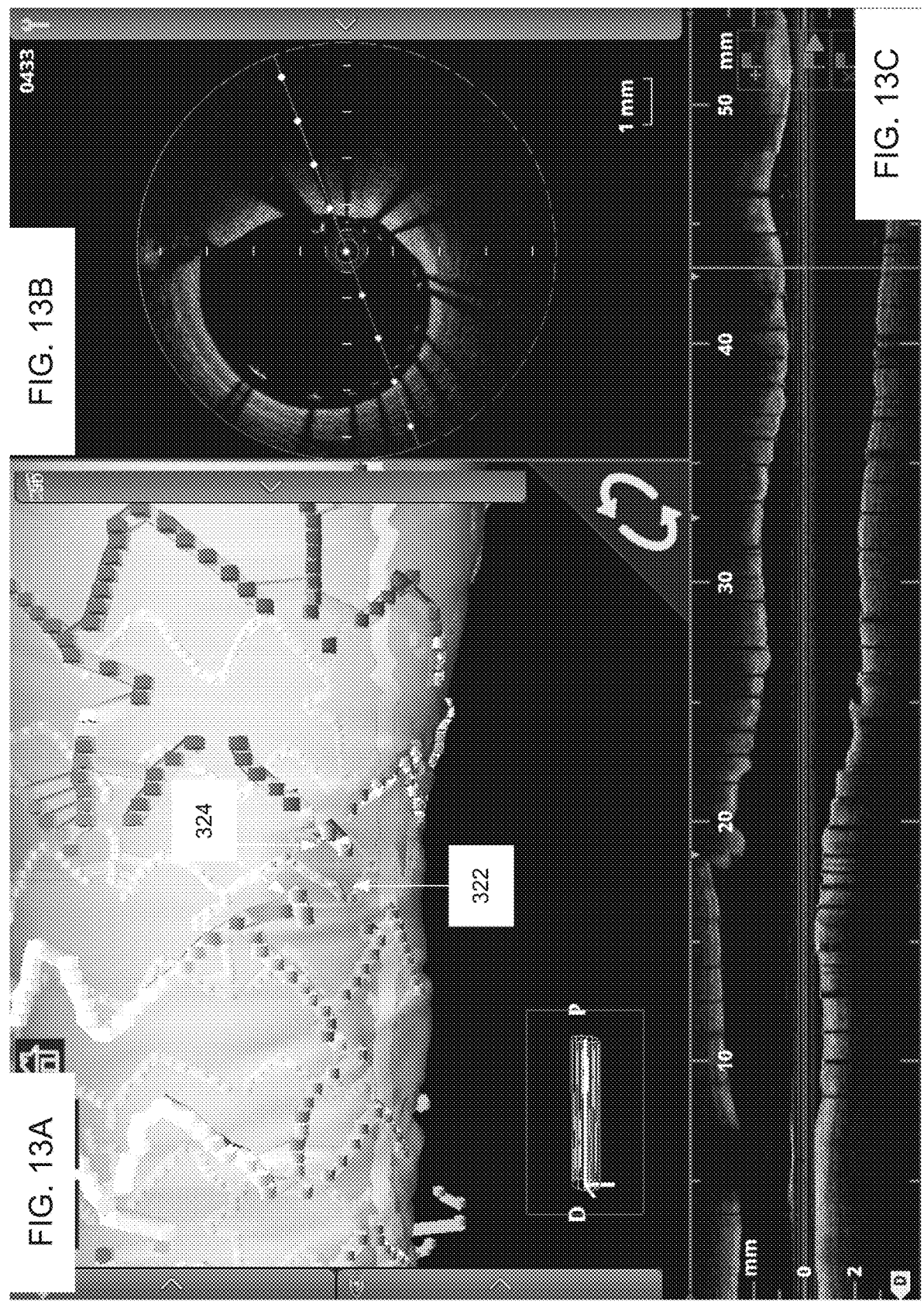

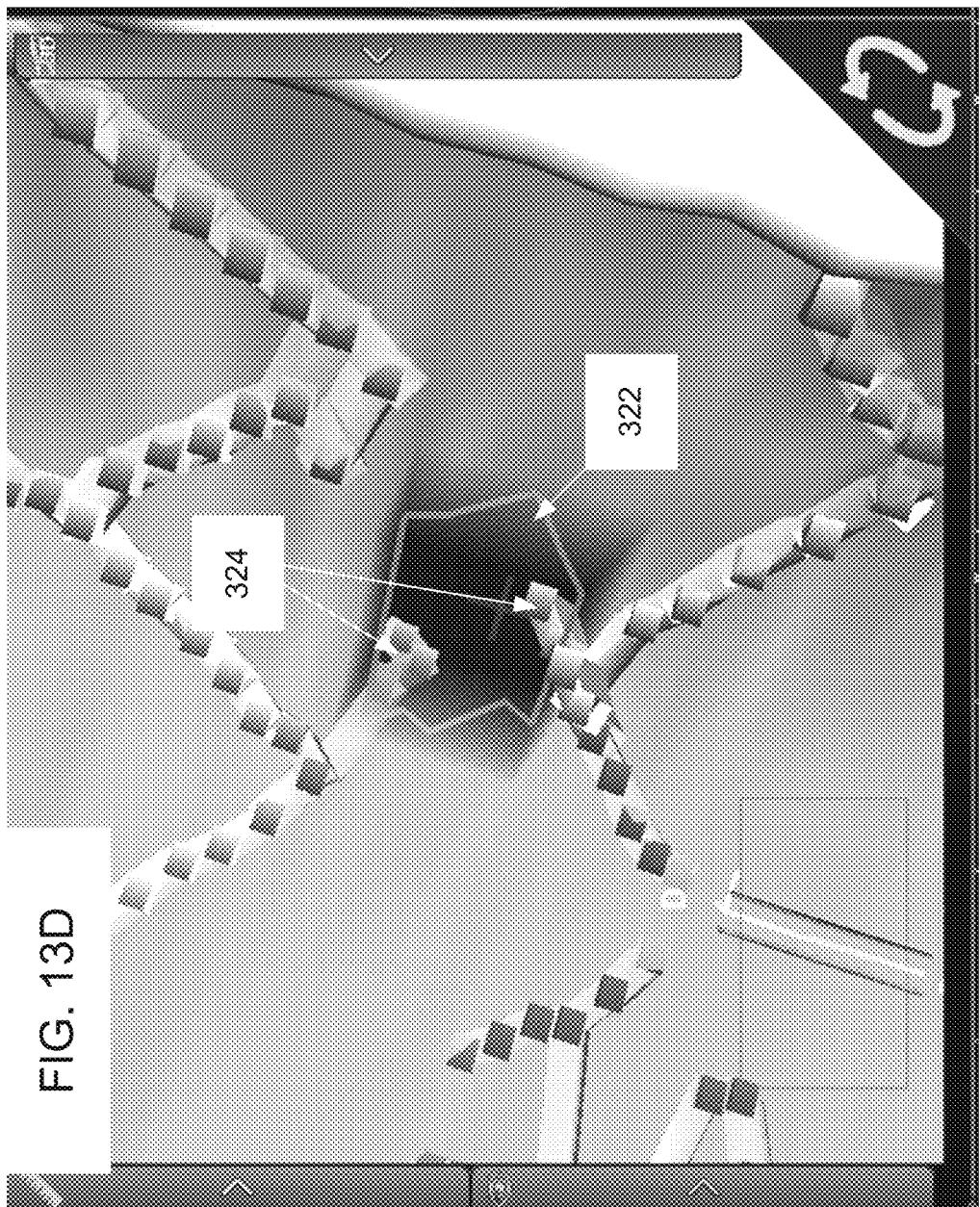

INTRAVASCULAR DATA VISUALIZATION AND INTERFACE SYSTEMS AND METHODS

CROSS-REFERENCED TO RELATED APPLICATIONS

This application is a continuation of U.S. patent application Ser. No. 15/219,197 filed on Jul. 25, 2016, which claims the benefit of priority under 35 U.S.C. 119€ from the United States Provisional Application No. 62/196,997 filed on Jul. 25, 2015, the disclosures of which are herein incorporated by reference in their entirety.

FIELD OF THE INVENTION

The disclosure relates generally to intravascular measurements and feature detection and related diagnostic methods and devices.

BACKGROUND

Coronary artery disease is one of the leading causes of death worldwide. The ability to better diagnose, monitor, and treat coronary artery diseases can be of life saving importance. Intravascular optical coherence tomography (OCT) is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs. This level of detail made possible with OCT allows a clinician to diagnose as well as monitor the progression of coronary artery disease. OCT images provide high-resolution visualization of coronary artery morphology and can be used alone or in combination with other information such as angiography data and other sources of subject data to aid in diagnosis and planning such as stent delivery planning OCT imaging of portions of a patient's body provides a useful diagnostic tool for doctors and others. For example, imaging of coronary arteries by intravascular OCT may reveal the location of a narrowing or stenosis. This information helps cardiologists to choose between an invasive coronary bypass surgery and a less invasive catheter-based procedure such as angioplasty or stent delivery. Although a popular option, stent delivery has its own associated risks.

A stent is a tube-like structure that often is formed from a mesh. It can be inserted into a vessel and expanded to counteract a stenotic condition that constricts blood flow. Stents typically are made of a metal or a polymer scaffold. They can be deployed to the site of a stenosis via a catheter. During a cardiovascular procedure, a stent can be delivered to the stenotic site through a catheter via a guide wire, and expanded using a balloon. Typically, the stent is expanded using a preset pressure to enlarge the lumen of a stenosed vessel. Angiography systems, intravascular ultrasound systems, OCT systems, in combinations or alone can be used to facilitate stent delivery planning and stent deployment.

There are several factors that influence the patient outcome when deploying stents. In some procedures, the stent should be expanded to a diameter that corresponds to the diameter of adjacent healthy vessel segments. Stent overexpansion may cause extensive damage to the vessel, making it prone to dissection, disarticulation, and intra-mural hemorrhage. Stent under expansion may inadequately expand the vessel. If the portions of the stent fail to contact the vessel wall, the risk of thrombosis may increase. An underinflated or malapposed stent may fail to restore normal flow. Once a stent is installed, stent malapposition and under expansion of the stent can result in various problems. In addition, flow-limiting stenoses are often present near vascular side branches.

Side branches can be partially or completely occluded or "jailed" by stent struts. For example, this can occur when a stent is deployed in a main vessel to address a stenosis or other malady. Side branches are vital for carrying blood to downstream tissues. Thus, jailing can have an undesired ischemic impact. The ischemic effects of jailing are compounded when multiple side branches are impacted or when the occluded surface area of a single branch is significant.

There are other challenges associated with stent placements and related procedures. Visualizing a stent deployment relative to the wall of a blood vessel using an angiography system is challenging to undertake by inspection.

The present disclosure addresses these challenges and others.

SUMMARY

In part, the disclosure relates systems and methods for visualizing intravascular data such as detected side branches and detected stent struts. The data can be obtained using an intravascular data collection probe. The probe can be pulled back through a blood vessel and data can be collected with respect thereto. In one embodiment, the probe is an optical probe such as an optical coherence tomography (OCT) probe. In one embodiment, the probe is an intravascular ultrasound probe (IVUS) such as an optical coherence tomography probe. Stents can be visualized relative to side branches in various embodiments of the disclosure. This is an important feature as it is typically the case that during stent deployment it is desirable to avoid stenting a side branch. The systems and methods described herein facilitate visualization of stents in side branches using various user interface and representations of stent struts and side branches based upon the detection of these features in the intravascular data collected.

In part, the disclosure relates to intravascular data collection systems and the software-based visualization and display of intravascular data relating to detected side branches and detected stent struts. Levels of stent malapposition can be defined using a user interface such as a slider, toggle, button, field, or other interface to specify how indicia are displayed relative to detected stent struts. In addition, the disclosure relates to methods to automatically provide a two or three-dimensional visualization suitable for assessing side branch and/or guide wire location during stenting. The method can use one or more a computed side branch location, a branch takeoff angle, one or more stent strut locations, and one or more lumen contours.

In part, the disclosure relates systems and methods for stent planning or otherwise to generate and display diagnostic information of interest. The disclosure also relates to the generation of various indicators and the integration of them relative to displays of image data. As an example, a longitudinal indicator such as an apposition bar can be used alone or in conjunction with a stent strut indicator and overlaid on angiography frames co-registered with an intravascular data set such as a set of OCT scan lines or images generated with respect thereto for diagnostic processes such as stent planning.

In part, the disclosure relates to systems and methods for displaying the results of data analysis applied to an intravascular data set to the user of an intravascular data collection system and on angiography system in one embodiment. In part, this disclosure describes a graphic user interface (GUI) that provides user interface and graphic data representations that can be applied to one or more generated images of a vessel or angiography images such that regions of interest such as areas of stent apposition and others are easy to find and understand on OCT and angiography images.

In part, the disclosure relates to a data collection system such as an intravascular data collection system suitable for use in cath lab such as an optical coherence tomography system. In part, the disclosure relates to a data collection system that includes a processor suitable for displaying intravascular image data. The image data displayed includes data or images generated based upon depth measurements. In one embodiment, the image data is generated using optical coherence tomography. The system can also display a user interface for display of intravascular information such as data relating to stent malapposition in a longitudinal mode on a per stent strut basis or as a bar having regions corresponding to stent, no stent, or stent apposition levels of potential interest for one or more stents in a vessel. One or more indicators such as longitudinal indicators, as a non-limiting example, can be generated in response to stent detection processing and lumen boundary detection and displayed relative to angiography, OCT, and IVUS images. These can be viewed by a user to plan stent delivery and to inflate or adjust a stent delivery by reviewing a co-registered OCT image and an angiography image with the relevant indicators of interest.

The present disclosure relates, in part, to computer-based visualization of stent position within a blood vessel and one or more viewing angles or orientations relating to one or both of a guidewire and a side branch. A stent can be visualized using OCT data and subsequently displayed as stent struts or portions of a stent as a part of a one or more graphic user interface(s) (GUI). A side branch and a guidewire can likewise be detected and displayed. In one embodiment, the disclosure provides software-based methods that can include computer algorithms that visualize detected intravascular features and display them in an optimized or optimal manner suitable to enhance their diagnostic value to an end user. The GUI can include one or more views of a blood vessel generated using OCT distance measurements and oriented in a position relative to a side branch or a guide wire to increase the diagnostic value or ease of use for an end user.

In part, the disclosure relates to a method of visualizing intravascular information obtained using an intravascular data collection probe. The method includes receiving intravascular data for a blood vessel, the data comprising a plurality of image frames; storing the intravascular data in a memory device of an intravascular data collection system; detecting one or more side branches on a per image frame basis; detecting a lumen on a per image frame basis; determining a first viewing angle for at least one of the side branch or lumen; and displaying a three-dimensional visualization for at least one of the side branch or lumen. In one embodiment, the lumen is a lumen boundary. In one embodiment, a lumen contour and a lumen boundary are interchangeable.

In one embodiment, the method further includes displaying a three-dimensional fly through relative to at least one of the side branch or lumen. In one embodiment, the intravascular data is optical coherence tomography data. In one embodiment, each image frame includes a set of scan lines. In one embodiment, the method further includes detecting a plurality of stent struts. In one embodiment, the method further includes detecting one or more guide wires.

In one embodiment, the method further includes determining a second viewing angle for the plurality of stents struts. In one embodiment, the method further includes determining a third viewing angle for the one or more guidewire. In one embodiment, the three-dimensional visualization is oriented at the first viewing angle. In one embodiment, the three-dimensional fly through is user controllable in one or more directions using an input device.

In one embodiment, the method further includes determining side branch arc of lumen contour; estimating side branch orientation by fitting a cylinder constrained by side branch arc; and selecting orientation of fitted cylinder. In one embodiment, the method further includes determining a mid-frame of image frames of intravascular data, determine mid-arc position on the mid frame; and set initial camera position for three-dimensional view to orient towards intravascular imaging probe for the mid frame.

In part, the disclosure relates to processor-based system for controlling stent apposition thresholds based on user inputs. The system includes one or more memory devices; and a computing device in communication with the one or more memory devices, wherein the one or more memory devices comprise instructions executable by the computing device to cause the computing device to: display a user interface comprising a stent strut apposition threshold control, the control comprising a user selectable input; store a user input stent strut apposition threshold in the one or more memory devices; detect one or more stents in an intravascular data set, the intravascular data set collected using an intravascular probe; display the one or more stents and one or more indicia associated with the one or more stents, wherein the indicia indicates a level of stent strut apposition, the level stent strut apposition determined using the user selectable input. In one embodiment, the stent strut apposition threshold control is a slider.

In one embodiment, the user selectable input is one or more values of the slider. In one embodiment, the indicia is one or more colors. In one embodiment, the slider is configured to define three apposition thresholds. In one embodiment, the stent strut apposition threshold control measures stent strut apposition relative to a front face of a stent strut. In one embodiment, the stent strut stent apposition threshold control is selected from the group consisting of a form fillable field; a button; a toggle control; a dial, and a numerical selection input.

BRIEF DESCRIPTION OF DRAWINGS

The figures are not necessarily to scale, emphasis instead generally being placed upon illustrative principles. The figures are to be considered illustrative in all aspects and are not intended to limit the disclosure, the scope of which is defined only by the claims.

FIG. 4A is a side view of a three-dimensional rendering of a main vessel having a side branch, with a stent and multiple guidewires deployed in the main vessel according to an illustrative embodiment of the disclosure.

FIG. 4B is a fly-through three-dimensional rendering of a side branch lumen, with the virtual camera angle oriented along the longitudinal axis of the side branch as shown in FIG. 3A according to an illustrative embodiment of the disclosure.

FIG. 4C is a fly-through three-dimensional rendering of a main vessel lumen, with the virtual camera angle oriented along the longitudinal axis of the main vessel as shown in FIG. 3A according to an illustrative embodiment of the disclosure.

FIG. 9A is a side view of a three-dimensional rendering of a blood vessel according to an illustrative embodiment of the disclosure.

FIG. 9B is a cross-sectional B-mode OCT intravascular image according to an illustrative embodiment of the disclosure.

FIG. 9C is a longitudinal L-mode OCT intravascular image according to an illustrative embodiment of the disclosure.

FIG. 10A is a side view of a three-dimensional rendering of a blood vessel showing jailed side branches according to an illustrative embodiment of the disclosure.

FIG. 10B is a cross-sectional B-mode OCT intravascular image according to an illustrative embodiment of the disclosure.

FIG. 10C is a longitudinal L-mode OCT intravascular image according to an illustrative embodiment of the disclosure.

FIG. 11A is a fly-through three-dimensional rendering of a blood vessel according to an illustrative embodiment of the disclosure.

FIG. 11B is a cross-sectional B-mode OCT intravascular image according to an illustrative embodiment of the disclosure.

FIG. 11C is a longitudinal L-mode OCT intravascular image according to an illustrative embodiment of the disclosure.

FIG. 13A is a side view of a three-dimensional rendering of a blood vessel showing a liberated side branch according to an illustrative embodiment of the disclosure.

FIG. 13B is a cross-sectional B-mode OCT intravascular image according to an illustrative embodiment of the disclosure.

FIG. 13C is a longitudinal L-mode OCT intravascular image according to an illustrative embodiment of the disclosure.

FIG. 13D is a zoomed view of FIG. 13A, showing the ostium and a cleaved stent strut according to an illustrative embodiment of the disclosure.

DETAILED DESCRIPTION

Figure 1:
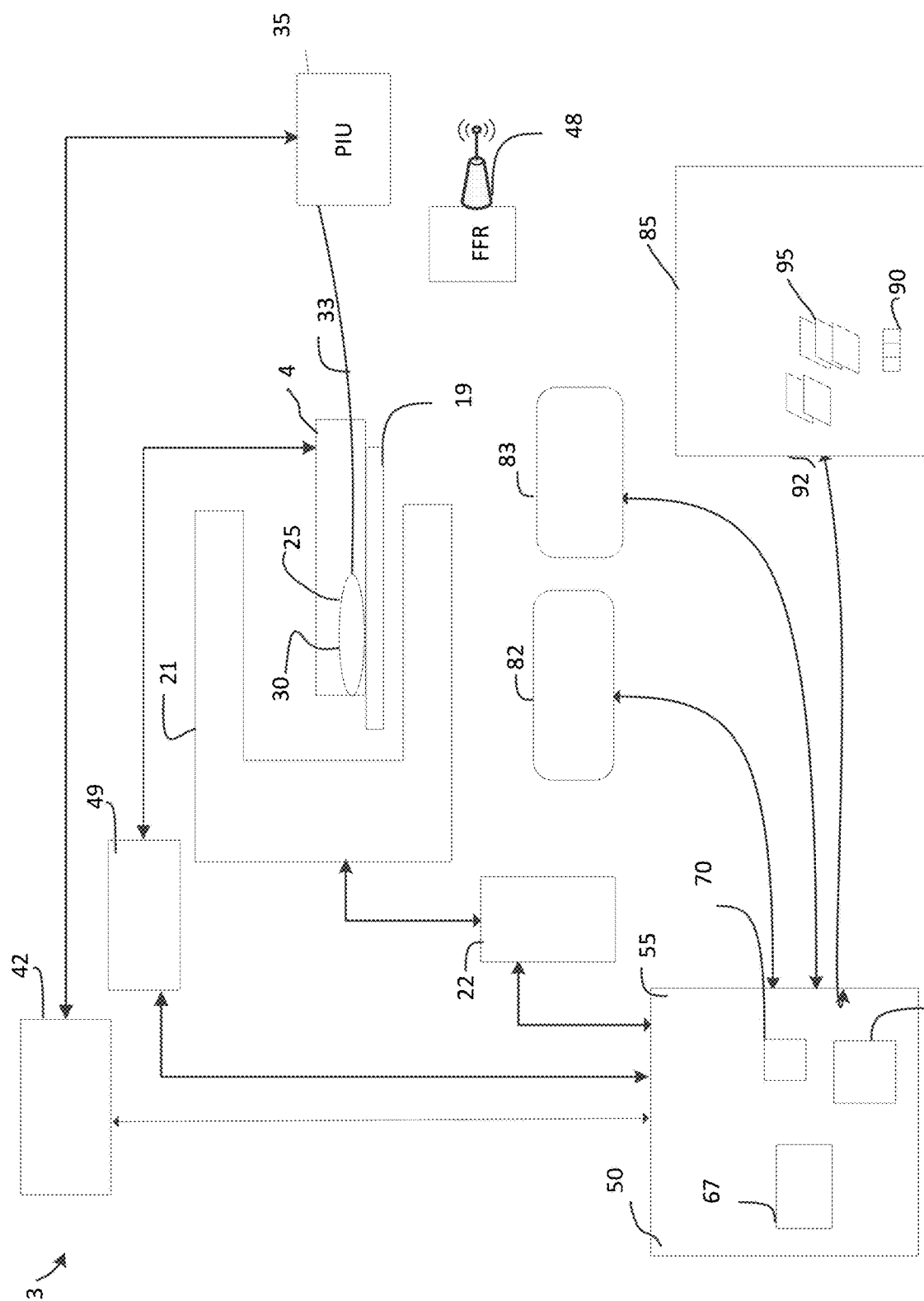
FIG. 1 shows a schematic diagram of an intravascular imaging and data collection system in accordance with an illustrative embodiment of the disclosure.

In part, the disclosure relates systems and methods for visualizing intravascular data such as detected side branches and detected stent struts. The data can be obtained using an intravascular data collection probe. The probe can be pulled back through a blood vessel and data can be collected with respect thereto. Such pullbacks and the associated data collection are used to plan stent deployment or evaluate deployed stents. The resulting intravascular data from a pullback can be used in various ways such as to visualize various blood vessel regions, features, and stents deployed in relation thereto.

Stents can be visualized relative to side branches in various embodiments of the disclosure. This is an important feature as it is typically the case that during stent deployment it is desirable to avoid stenting a side branch. The systems and methods described herein facilitate visualization of stents in side branches using various user interface and representations of stent struts and side branches based upon the detection of these features in the intravascular data collected.

In part, the disclosure relates to intravascular data collection systems, such as OCT, IVUS, and other imaging modalities and the generation and visualization of diagnostic information such as stent malapposition or other indicators. The disclosure also relates to various user interface features that allow a user to specify parameters and thresholds of interest such as the thresholds or parameters used to evaluate when a stent is malapposed and/or the degree of apposition.

The parameters can be used to adjust or modify how and when indicators such as graphical elements suitable for indicating diagnostic information of interest such as apposition levels and stent position relative to regions in the blood vessel. In one embodiment, the regions can include detected side branches. Stent strut indicators can also be used.

Suitable diagnostic information can include stent apposition information such as the relative to a vessel wall or lumen boundary and other intravascular diagnostic information or other information generated to facilitate stent delivery planning. The system includes a processor in communication with the graphical user interface and configured to send commands to the graphical user interface. One or more software programs are used to perform one or more of the following: display indicators such as color-coded stent struts or symbols or other indicia displayed at the location of detected stent struts, stent position and orientation relative to a side branch and stent apposition levels based upon a user specified criteria for when apposition of a stent should be displayed.

Also disclosed herein are systems and methods for visualizing stents and other medical devices relative to side branches to avoid the jailing thereof vessels. One or more software modules can be used to detect side branch locations, lumen contours, and stent strut positions. One or more viewing angles or orientations can be generated to help a user visualize when side branch jailing may occur.

It may be necessary to open a group of cells in a deployed stent using a balloon in order to improve blood flow in the jailed side branch. The balloon guidewire typically is crossed into the jailed side branch ostium in as distal (e.g., downstream) a position as possible. Obtaining a distal guidewire position will lead to the stent struts being pushed to the proximal (e.g., upstream) side of the side branch ostium, which minimizes flow disruptions at the higher-flow distal side of the ostium. Clear, rapid visualization of guidewire position in relation to the stent and side branch is therefore clinically advantageous.

FIG. 1 includes a system suitable for performing various steps of the disclosure such as displaying detected stent struts, side branches, and guidewires and associated indicia and orientation angles relating thereto. Various user interface features are described herein to view and assess a visual representation of intravascular information. These user interfaces can include one or more moveable elements that can be controlled by a user with a mouse, joystick, or other control and can be operated using one or more processors and memory storage elements. For example, the sliders of FIGS. 15A-15C can be so controlled.

During a stent delivery planning procedure, the levels and location of apposition the user can refer to OCT and annotated angiography to further expand or move a stent as part of delivery planning. These system features and methods can be implemented using system 5 shown in FIG. 1.

FIG. 1 shows a system 5 which includes various data collection subsystems suitable for collecting data or detecting a feature of or sensing a condition of or otherwise diagnosing a subject 10. In one embodiment, the subject is disposed upon a suitable support 12 such as table bed to chair or other suitable support. Typically, the subject 10 is the human or another animal having a particular region of interest 25.

The data collection system 5 includes a noninvasive imaging system such as a nuclear magnetic resonance, x-ray, computer aided tomography, or other suitable noninvasive imaging technology. As shown as a non-limiting example of such a noninvasive imaging system, an angiography system 20 such as suitable for generating cines is shown. The angiography system 20 can include a fluoroscopy system. Angiography system 20 is configured to noninvasively image the subject 10 such that frames of angiography data, typically in the form of frames of image data, are generated while a pullback procedure is performed using a probe 30 such that a blood vessel in region 25 of subject 10 is imaged using angiography in one or more imaging technologies such as OCT or IVUS, for example.

The angiography system 20 is in communication with an angiography data storage and image management system 22, which can be implemented as a workstation or server in one embodiment. In one embodiment, the data processing relating to the collected angiography signal is performed directly on the detector of the angiography system 20. The images from system 20 are stored and managed by the angiography data storage and image management 22.

In one embodiment system server 50 or workstation 85 handle the functions of system 22. In one embodiment, the entire system 20 generates electromagnetic radiation, such as x-rays. The system 20 also receives such radiation after passing through the subject 10. In turn, the data processing system 22 uses the signals from the angiography system 20 to image one or more regions of the subject 10 including region 25.

As shown in this particular example, the region of interest 25 is a subset of the vascular or peripherally vascular system such as a particular blood vessel. This can be imaged using OCT. A catheter-based data collection probe 30 is introduced into the subject 10 and is disposed in the lumen of the particular blood vessel, such as for example, a coronary artery. The probe 30 can be a variety of types of data collection probes such as for example an OCT probe, an FFR probe, an IVUS probe, a probe combining features of two or more of the foregoing, and other probes suitable for imaging within a blood vessel. The probe 30 typically includes a probe tip, one or more radiopaque markers, an optical fiber, and a torque wire. Additionally, the probe tip includes one or more data collecting subsystems such as an optical beam director, an acoustic beam director, a pressure detector sensor, other transducers or detectors, and combinations of the foregoing.

For a probe that includes an optical beam director, the optical fiber 33 is in optical communication with the probe with the beam director. The torque wire defines a bore in which an optical fiber is disposed. In FIG. 1, the optical fiber 33 is shown without a torque wire surrounding it. In addition, the probe 30 also includes the sheath such as a polymer sheath (not shown) which forms part of a catheter. The optical fiber 33, which in the context of an OCT system is a portion of the sample arm of an interferometer, is optically coupled to a patient interface unit (PIU) 35 as shown.

The patient interface unit 35 includes a probe connector suitable to receive an end of the probe 30 and be optically coupled thereto. Typically, the data collection probes 30 are disposable. The PIU 35 includes suitable joints and elements based on the type of data collection probe being used. For example a combination OCT and IVUS data collection probe requires an OCT and IVUS PIU. The PIU 35 typically also includes a motor suitable for pulling back the torque wire, sheath, and optical fiber 33 disposed therein as part of the pullback procedure. In addition to being pulled back, the probe tip is also typically rotated by the PIU 35. In this way, a blood vessel of the subject 10 can be imaged longitudinally or via cross-sections. The probe 30 can also be used to measure a particular parameter such as a fractional flow reserve (FFR) or other pressure measurement.

In turn, the PIU 35 is connected to one or more intravascular data collection systems 40. The intravascular data collection system 40 can be an OCT system, an IVUS system, another imaging system, and combinations of the foregoing. For example, the system 40 in the context of probe 30 being an OCT probe can include the sample arm of an interferometer, the reference arm of an interferometer, photodiodes, a control system, and patient interface unit. Similarly, as another example, in the context of an IVUS system, the intravascular data collection system 40 can include ultrasound signal generating and processing circuitry, noise filters, rotatable joint, motors, and interface units. In one embodiment, the data collection system 40 and the angiography system 20 have a shared clock or other timing signals configured to synchronize angiography video frame time stamps and OCT image frame time stamps.

In addition to the invasive and noninvasive image data collection systems and devices of FIG. 1, various other types of data can be collected with regard to region 25 of the subject and other parameters of interest of the subject. For example, the data collection probe 30 can include one or more pressure sensors such as for example a pressure wire. A pressure wire can be used without the additions of OCT or ultrasound components. Pressure readings can be obtained along the segments of a blood vessel in region 25 of the subject 10.

Such readings can be relayed either by a wired connection or via a wireless connection. As shown in a fractional flow reserve FFR data collection system, a wireless transceiver 47 is configured to receive pressure readings from the probe 30 and transmit them to a system to generate FFR measurements or more locations along the measured blood vessel. One or more displays 82, 83 can also be used to show an angiography frame of data, an OCT frame, user interfaces for OCT and angiography data and other controls and features of interest.

The intravascular image data such as the frames of intravascular data generated using the data collection probe 30 can be routed to the data collection processing system 40 coupled to the probe via PIU 35. The noninvasive image data generated using angiography system 22 can be transmitted to, stored in, and processed by one or more servers or workstations such as the co-registration server 50 workstation 85. A video frame grabber device 55 such as a computer board configured to capture the angiography image data from system 22 can be used in various embodiments.

In one embodiment, the server 50 includes one or more co-registration software modules 67 that are stored in memory 70 and are executed by processor 80. The server 50 can include other typical components for a processor-based computing server. Alternatively, more databases such as database 90 can be configured to receive image data generated, parameters of the subject, and other information generated, received by or transferred to the database 90 by one or more of the systems devices or components shown in FIG. 1. Although database 90 is shown connected to server 50 while being stored in memory at workstation 85, this is but one exemplary configuration. For example, the software modules 67 can be running on a processor at workstation 85 and the database 90 can be located in the memory of server 50. The device or system use to run various software modules are provided as examples. In various combinations the hardware and software described herein can be used to obtain frames of image data, process such image data, and register such image data.

As otherwise noted herein, the software modules 67 can include software such as preprocessing software, transforms, matrices, and other software-based components that are used to process image data or respond to patient triggers to facilitate co-registration of different types of image data by other software-based components 67 or to otherwise perform such co-registration. The modules can include lumen detection using a scan line based or image based approach, stent detection using a scan line based or image based approach, indicator generation, apposition bar generation for stent planning, guidewire shadow indicator to prevent confusion with dissention, side branches and missing data, and others.

The database 90 can be configured to receive and store angiography image data 92 such as image data generated by angiography system 20 and obtained by the frame grabber 55 server 50. The database 90 can be configured to receive and store OCT image data 95 such as image data generated by OCT system 40 and obtained by the frame grabber 55 server 50.

In addition, the subject 10 can be electrically coupled via one or more electrodes to one more monitors such as, for example, monitor 49. Monitor 49 can include without limitation an electrocardiogram monitor configured to generate data relating to cardiac function and showing various states of the subject such as systole and diastole. Knowing the cardiac phase can be used to assist the tracking of vessel centerlines, as the geometry of the heart, including the coronary arteries, is approximately the same at a certain cardiac phase, even over different cardiac cycles.

Hence, if the angiography data spans a few cardiac cycles, a first-order matching of vessel centerline at the same cardiac phase may assist in tracking the centerlines throughout the pullback. In addition, as most of the motion of the heart occurs during the systole, vessel motion is expected to be higher around the systole, and damp towards the diastole. This provides data to one or more software modules as an indication of the amount of motion expected between consecutive angiography frames. Knowledge of the expected motion can be used by one or more software modules to improve the tracking quality and vessel centerline quality by allowing adaptive constraints based on the expected motion.

The use of arrow heads showing directionality in a given figure or the lack thereof are not intended to limit or require a direction in which information can flow. For a given connector, such as the arrows and lines shown connecting the elements shown in FIG. 1, for example, information can flow in one or more directions or in only one direction as suitable for a given embodiment. The connections can include various suitable data transmitting connections such as optical, wire, power, wireless, or electrical connections.

One or more software modules can be used to process frames of angiography data received from an angiography system such as system 22 shown in FIG. 1. Various software modules that can include without limitation software, a component thereof, or one or more steps of a software-based or processor executed method can be used in a given embodiment of the disclosure.

Intravascular Data Visualization

In one aspect, a computer-implemented method is provided to create an optimal three-dimensional visualization for assessing an intravascular treatment site. In various embodiments, the method includes automatically determining an optimal camera location and view perspective based on side branch morphology, to facilitate visualization of the treatment site. The method can include detection of medical devices (e.g. stents) and related deployment devices (e.g., guidewires). This feature is particularly useful for bifurcation stenting, to identify jailed side branches and to assist clinicians in modifying stent cells to alleviate obstructions. The various methods described herein relating to side branch, guide wire and other forms of intravascular data visualization can be implemented using a software module 67 of an intravascular data collection system performing one or more of the steps described herein.

Figure 2:
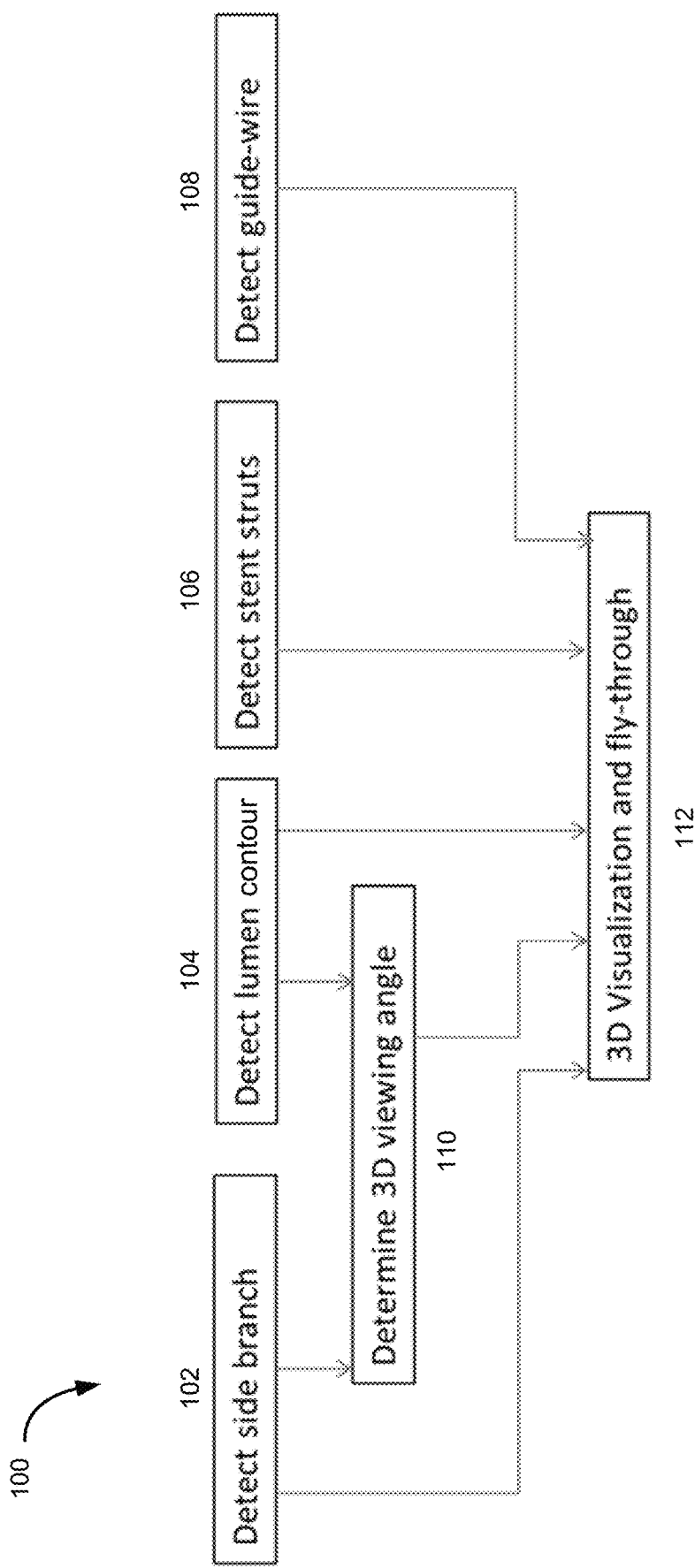
FIG. 2 is a flow chart illustrating a framework for visualization of a stent in a vessel side branch according to an illustrative embodiment of the disclosure.

Referring to FIG. 2, in one embodiment the computer-implemented method 100 includes one or more of the following data collection steps: side branch detection 102, lumen contour detection 104, stent strut detection 106, and guidewire detection 108. Side branch detection and lumen detection can include the sub-step of determining the optimal viewing angle 110 based on the angle at which the side branch joins the main vessel. As described in more detail herein, these inputs are used to create a three-dimensional visualization of the treatment site, such as a fly-through display. Different view angles include, by way of non-limiting example, side view, perspective view, top view, side branch fly-through, main vessel fly-through, and orthogonal ostium views.

Figure 3A:
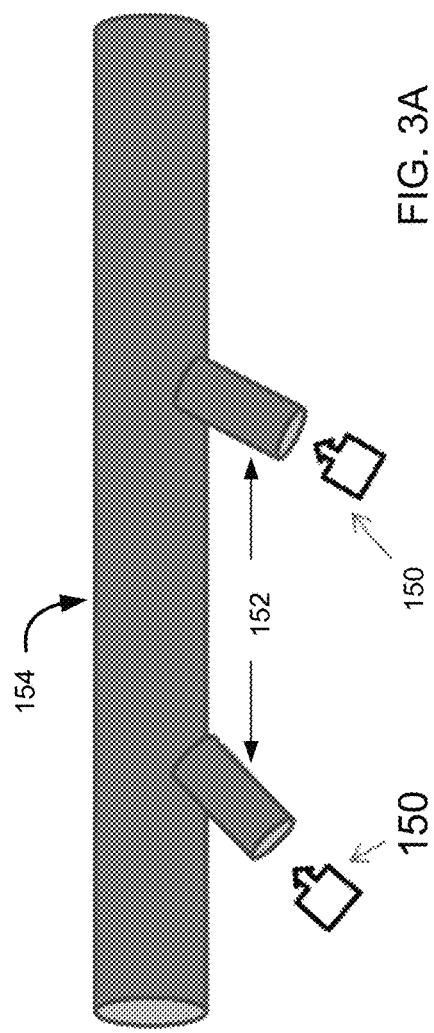
FIG. 3A is a schematic diagram illustrating virtual camera positioning for visualizing vessel side branches according to an illustrative embodiment of the disclosure.
Figure 3B:
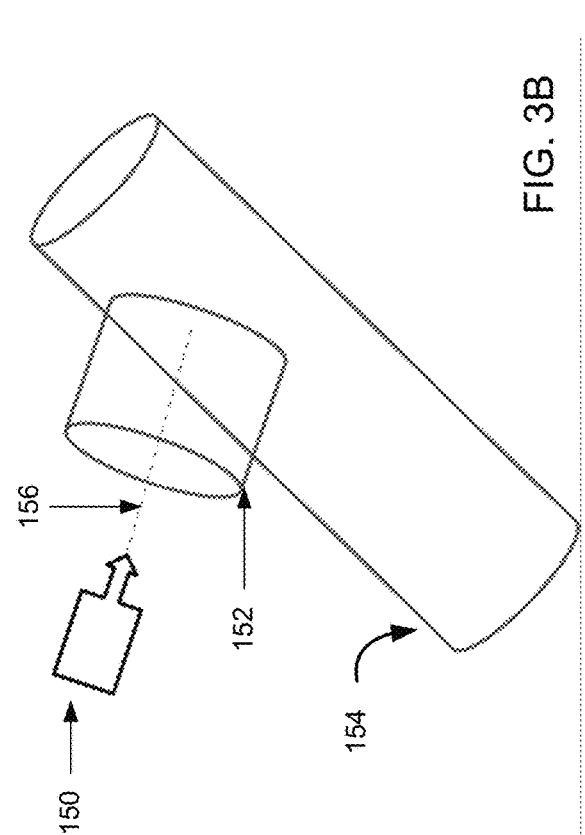
FIG. 3B is a schematic diagram illustrating a virtual camera position for visualizing a vessel side branch according to an illustrative embodiment of the disclosure.

Referring to FIG. 3A, in one embodiment a virtual camera 150 is generated for one or more side branches 152 in a main vessel 154. Virtual cameras are placed at appropriate viewing angles for visualizing, in three-dimensions, a side branch looking in the direction of the main vessel. Referring to FIG. 3B, in one mode of operation, the camera orientation 156 is selected to be parallel to the longitudinal axis of the side branch. Referring to FIG. 3C, in another mode, the camera orientation 156 is selected to be orthogonal to the surface of the main vessel 154 and/or orthogonal to the side branch ostium 158. These view angles are exemplary, and any suitable viewing angle can be used.

Figure 3D:
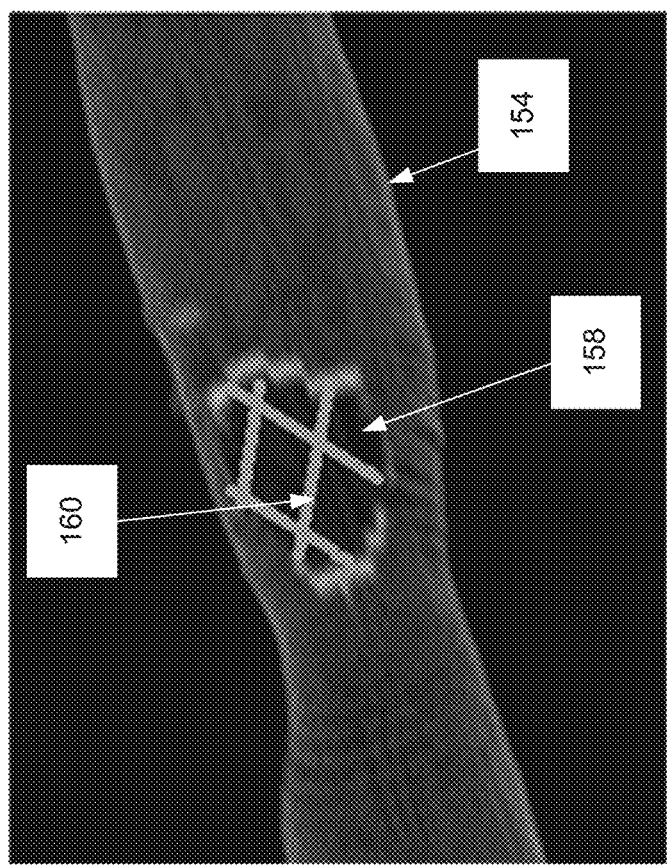
FIG. 3D is a three-dimensional rendering of stent struts jailing a vessel side branch ostium according to an illustrative embodiment of the disclosure.
Figure 3C:
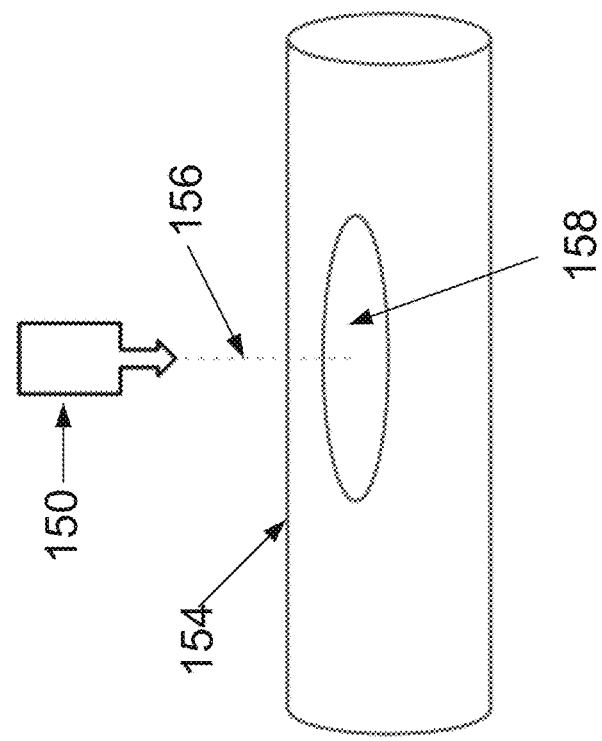
FIG. 3C is a schematic diagram illustrating a virtual camera position for orthogonal viewing of a side branch ostium according to an illustrative embodiment of the disclosure.

Referring to FIG. 3D, in another embodiment the user can visualize the stent struts 160 that cross the side branch ostium 158. For better viewing of the jailing stent struts, the side branch can be eliminated from the display so that the user can clearly visualize the ostium and stent struts crossing the ostium. In FIG. 3D, the virtual camera is orthogonal to the side branch ostium, looking through the ostium into the lumen of the main vessel where the stent is deployed.

FIG. 4A is a side view of a three-dimensional rendering of a main vessel 154 having a side branch 152. In this embodiment, the main vessel guidewire 164, side branch guidewire 166, and stent struts 160 are visible.

FIG. 4B is a three-dimensional rendering looking down side branch 152 (e.g., a fly-through) towards main vessel 154. In this embodiment, the camera 150b is oriented along the direction of the side branch angle as shown in FIG. 4A. The side branch guidewire 164, main vessel guidewire 166, and stent struts 160 are visible.

FIG. 4C is a three-dimensional fly-through down the main vessel 154. In this embodiment, the camera 150m is oriented along the longitudinal axis of the main branch as shown in FIG. 4A. The side branch guidewire 164, main vessel guidewire 166, and stent struts 160 are visible.

Figure 5A:
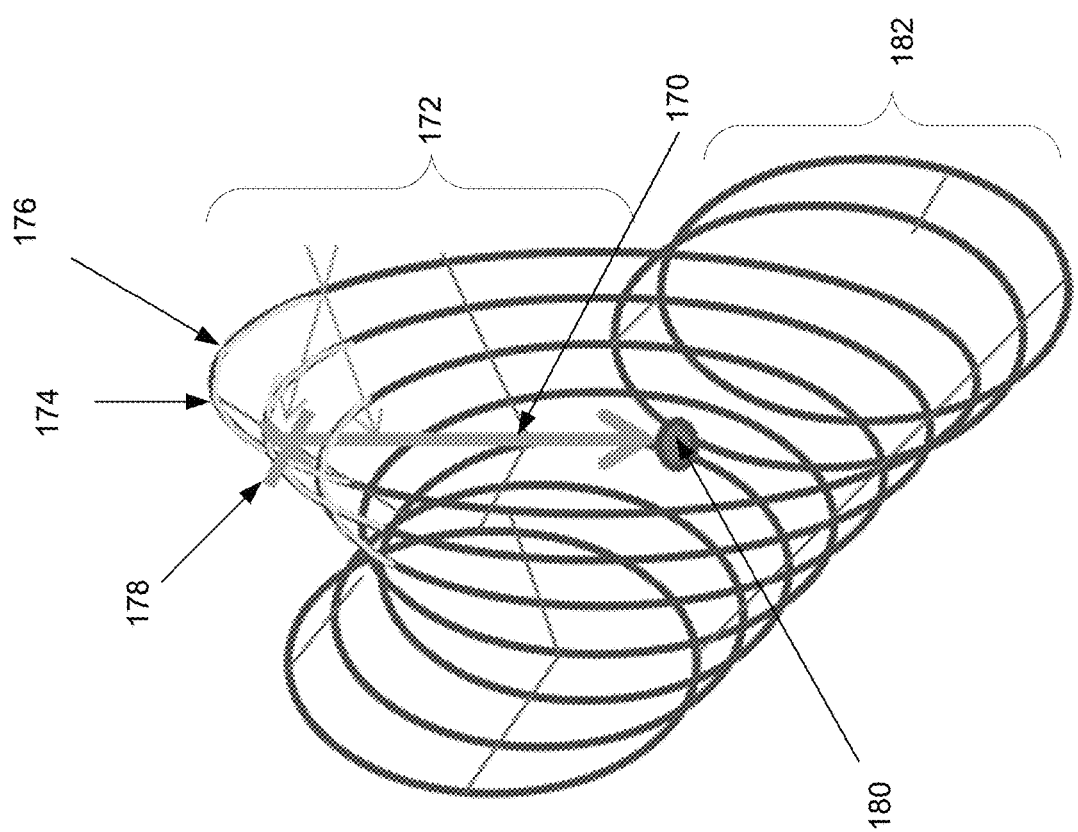
FIG. 5A is a schematic diagram showing virtual camera positioning using a mid-frame/mid-arc model according to an illustrative embodiment of the disclosure.

In various embodiments, the method can include the step of automatically identifying an initial camera position. Referring to FIG. 5A, in one embodiment, side branch orientation is estimated by finding the mid-frame 170, and the mid-arc position on the mid-frame in imaging data (e.g., OCT data). The mid-frame 170 is the center of side branch lumen 172 in a given imaging frame. The mid-arc 174 is the center of the arc defining the side branch lumen contour 176. In a preferred embodiment, the mid-arc position is used as the initial camera position 178—i.e., where the virtual camera is placed. The initial camera orientation—i.e., where the virtual camera is aimed—is then selected automatically. In a preferred embodiment, the camera is oriented towards the imaging catheter 180 for that mid-frame, to provide the clinician a view down the side branch lumen 172 towards the main vessel lumen 182. However, the camera can be oriented in any direction.

Figure 5B:
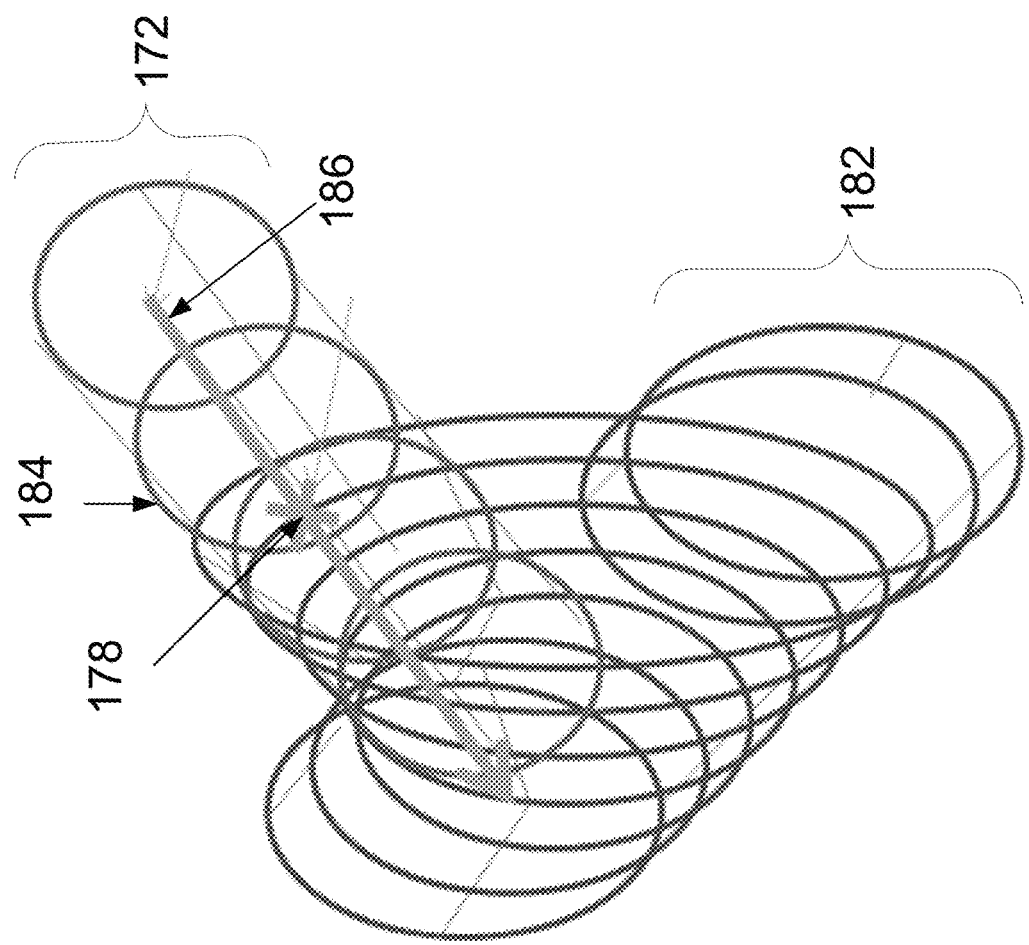
FIG. 5B is a schematic diagram showing virtual camera positioning using a cylinder model.

Referring to FIG. 5B, in another embodiment, camera positioning is determined by fitting a cylinder 184 to the side branch lumen 174. Side branch orientation 186 is then estimated using the arc of the cylinder 184, which is a proxy for the arc of the side branch lumen contour. In a preferred embodiment, the camera 178 is positioned along the axis of the side branch 186. The initial camera orientation is then selected automatically. In a preferred embodiment, the camera is automatically oriented down the cylinder axis 186 towards the main vessel lumen 182. However, the camera can be oriented in any direction.

The disclosure also provides computer-implemented methods for enhanced visualization of medical devices, such as guidewires and stents, on a user display. This enhanced visualization aids clinicians in evaluating a treatment site, adjusting deployed medical devices, and assessing whether further intervention is required. For example, it is particularly important for the clinician to understand when a guidewire is positioned inside (i.e., luminal) of a stent or outside (i.e., abluminal) of a stent. As another example, it is often necessary to open a group of cells in a deployed stent using a balloon in order to improve blood flow in the jailed side branch. The balloon guidewire typically is crossed into the jailed side branch ostium in as distal (e.g., downstream) a position as possible. Obtaining a distal guidewire position will lead to the stent struts being pushed to the proximal (e.g., upstream) side of the side branch ostium, which minimizes flow disruptions at the higher-flow distal side of the ostium.

Stent struts and guidewires can be detected automatically in imaging data and can be shown on a user display to provide the clinician with a comprehensive visualization of the treatment site. Stent struts and guidewires can be displayed in a visually distinct manner, such as by using different colors, to permit rapid interpretation by a clinician. In an embodiment, a guidewire can be shown in different colors according to its luminal/abluminal position relative to a stent. For example, an abluminal guidewire can be displayed in red as a warning and a luminal guidewire can be displayed in yellow. This visualization can help clarify the point at which a guidewire crosses over into a jailed branch, and can also help to alert the user to guidewires that have been inadvertently positioned abluminal of a stent section in the main branch.

In another embodiment, where multiple guidewires are used, the guidewires may each be shown in different colors, or they guidewires may be categorized by color. For example, a side branch guidewire may be shown in one color, and a main vessel guidewire may be shown in another color. In another embodiment, a guidewire can be shown in one color where it traverses the main vessel lumen and that portion of the same guidewire, which traverses a side branch, can be shown in a different color. In another embodiment, a guidewire can be shown in a different color where is crosses an ostium, or where it passes through a stent cell.

Similarly, the stent and/or some of all of the stent struts can be shown in different colors to indicate potential issues such as, for example, struts that jail a side branch. For example, struts crossing an ostium can be shown in red whereas struts adjacent a vessel wall can be shown in blue.

In another embodiment, a side branch ostium can be demarcated by visual indicia, such as polygon highlighting around the edges of the ostium. The visual indicia can be one color for an unobstructed ostium, and another color for an obstructed ostium.

Color-coding also can be applied to stent struts in order to clarify the position of stent struts relative to the virtual camera. In FIGS. 4A-4C, it can be difficult to appreciate which stents are located over the branch ostium versus which stents are located against the main vessel wall. However, referring to FIG. 3B, following automated detection of the individual struts and the vessel lumen, struts that are less relevant to visualization of wire re-crossing can be assigned a de-emphasizing color, such as grey or white, or can be removed altogether, while more relevant struts that jail the side branch can be assigned an emphasizing color, such as red.

Colors are only one example of visual indicia that can be used in accordance with the disclosure. For example, the indicia can be a bar, box, other any other suitable visualizable display element, symbol or icon. Preferably, the indicia demarcates the quantitatively conveys the extent of any side branch occlusion by, for example, color coding, shading, and/or varying opacity of the indicia.

Assessing Side Branch Obstruction

The invention also provides computer implemented methods for calculating and visualizing the degree of branch obstruction. Several methods can be used to calculate branch obstruction due to the presence of pathology (e.g., stenosis) or medical intervention (e.g., jailing).

Figure 6:
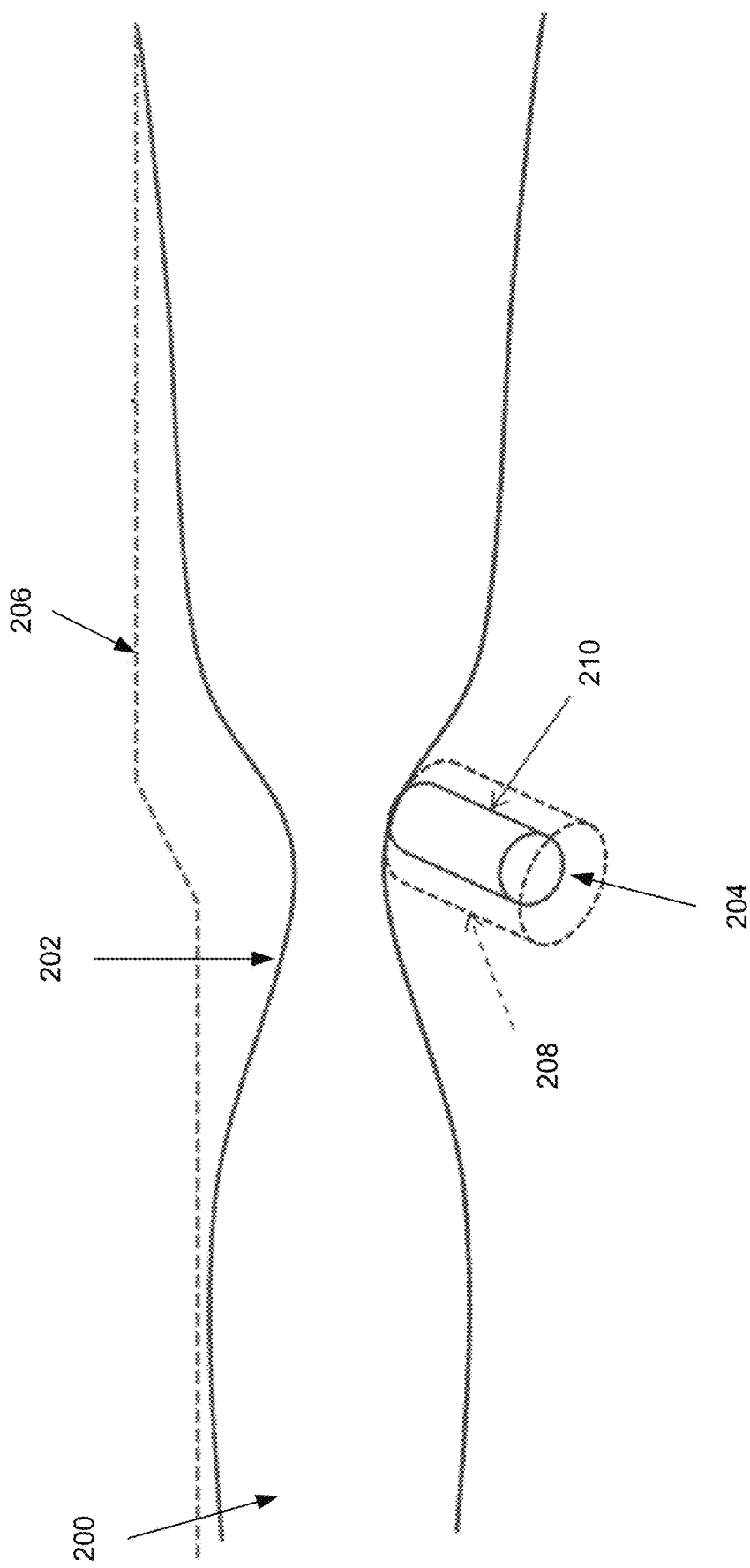
FIG. 6 is a schematic diagram illustrating side branch size estimations according to an illustrative embodiment of the disclosure.

In an embodiment, a reference vessel diameter method is used to assess side branch obstruction. FIG. 6 shows a main vessel 200 having a stenosis 202. A side branch 204 also is shown. A reference profile can be created for the main vessel 206 and/or a reference profile can be created for the side branch 208. Using the reference profile (dotted line) 208, an estimated branch diameter can be calculated by using distal and proximal reference profile diameters In one embodiment, the power law is given by the expression:

$$D_b^\varepsilon(i) = D^\varepsilon(i+1) - D^\varepsilon(i) \quad \text{(Eqn. 1)}$$

where D(i+1) is the proximal reference profile diameter and D(i) is the distal reference profile diameter; where $D_b(i)$ is the estimated true branch diameter; and ε is a power-law scaling exponent that has a value between 2.0 and 3.0 as determined empirically.

The difference between the estimated branch diameter and the actual branch diameter detected by OCT imaging provides the level of branch obstruction. In one embodiment, the level of branch obstruction is given by the expression:

$$D_{obstruction}(i) = D_b(i) - D_{OCT}(i) \quad \text{(Eqn. 2)}$$

where $D_b(i)$ is the estimated true branch diameter, and $D_{OCT}(i)$ is the actual branch diameter measured by OCT.

In an embodiment, a max diameter frames method is used to assess side branch obstruction. Instead of using a reference profile, the branch diameter is estimated using the maximum diameter in the main vessel segment distal and proximal to the current branch.

In an embodiment, a flow method is used to assess side branch obstruction. Using Virtual Flow Reserve (VFR) the flow going into each side branch can be estimated. The difference in flow down a given side branch due to the difference in OCT based branch diameter $Flow_{OCT}(i)$ and the true branch diameter $Flow_b(i)$ is an additional indication of the effect on flow due to the obstructed side branch. The true branch diameter can be calculated using one of the methods described above by either using the reference vessel profile or the max diameter frame in the distal and proximal segments. The flow method can be given as the following expression:

$$Flow_{obstruction}(i) = Flow_b(i) - Flow_{OCT}(i) \quad \text{(Eqn. 2)}$$

Figure 7:
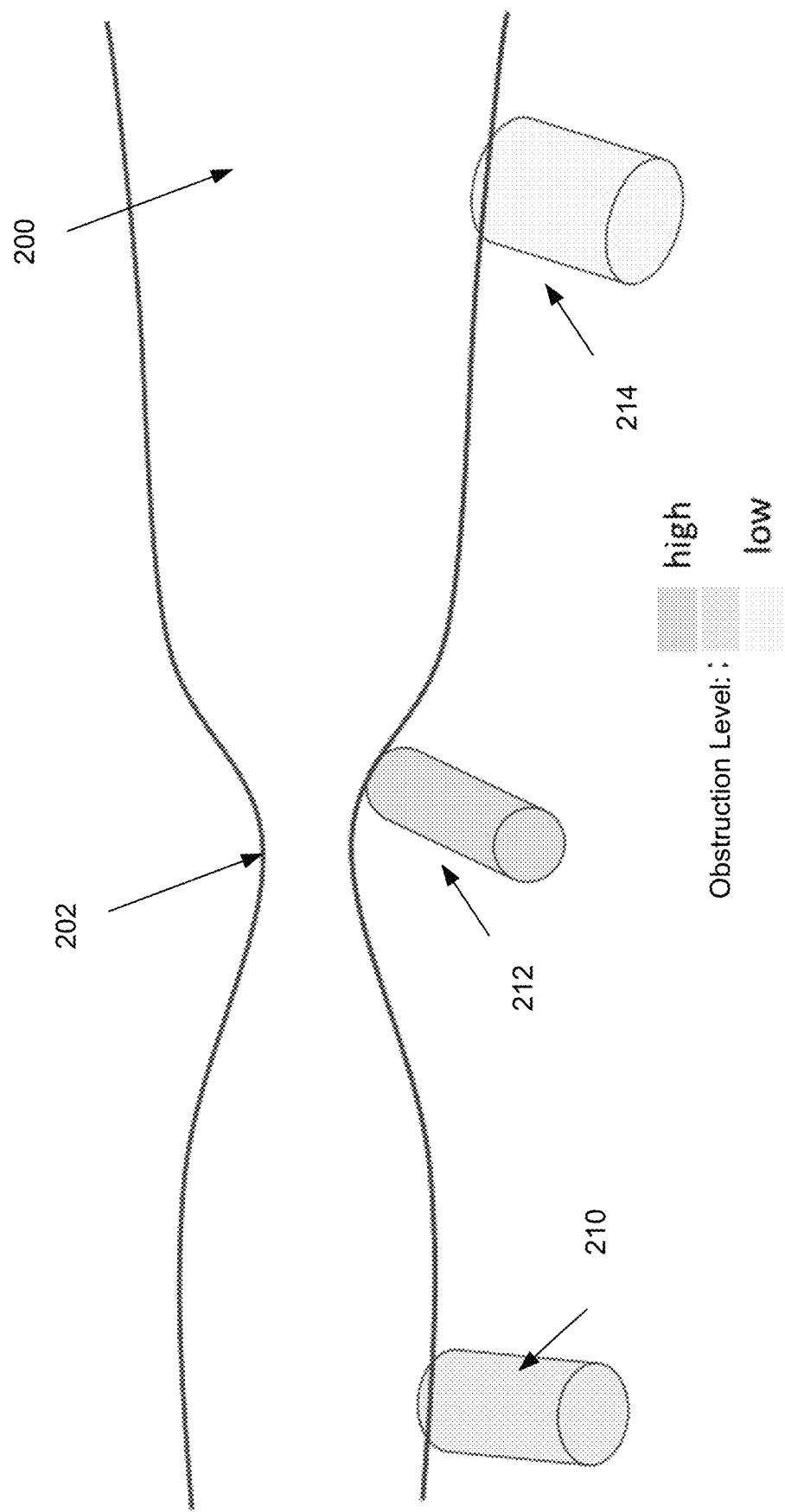
FIG. 7 is a schematic diagram displaying side branch location and color coding the degree of side branch occlusion according to an illustrative embodiment of the disclosure.

In various embodiments, side branch flow obstruction is represented on a user display using visual indicia, such as color-coding. The indicia can be coded to confer the level of side branch obstruction. These indicia can also be set based upon user input via a user interface. FIG. 7 is schematic diagram of an exemplary user display. The display shows a main vessel 200 having a stenosis 202 and three side branches 210, 212, 214. A highly obstructed side branch 212 is demarcated by different indicia (e.g., red color) than a moderately obstructed side branch 210 (e.g., orange color) and a low/non-obstructed side branch 214 (e.g., yellow color).

Figure 8:
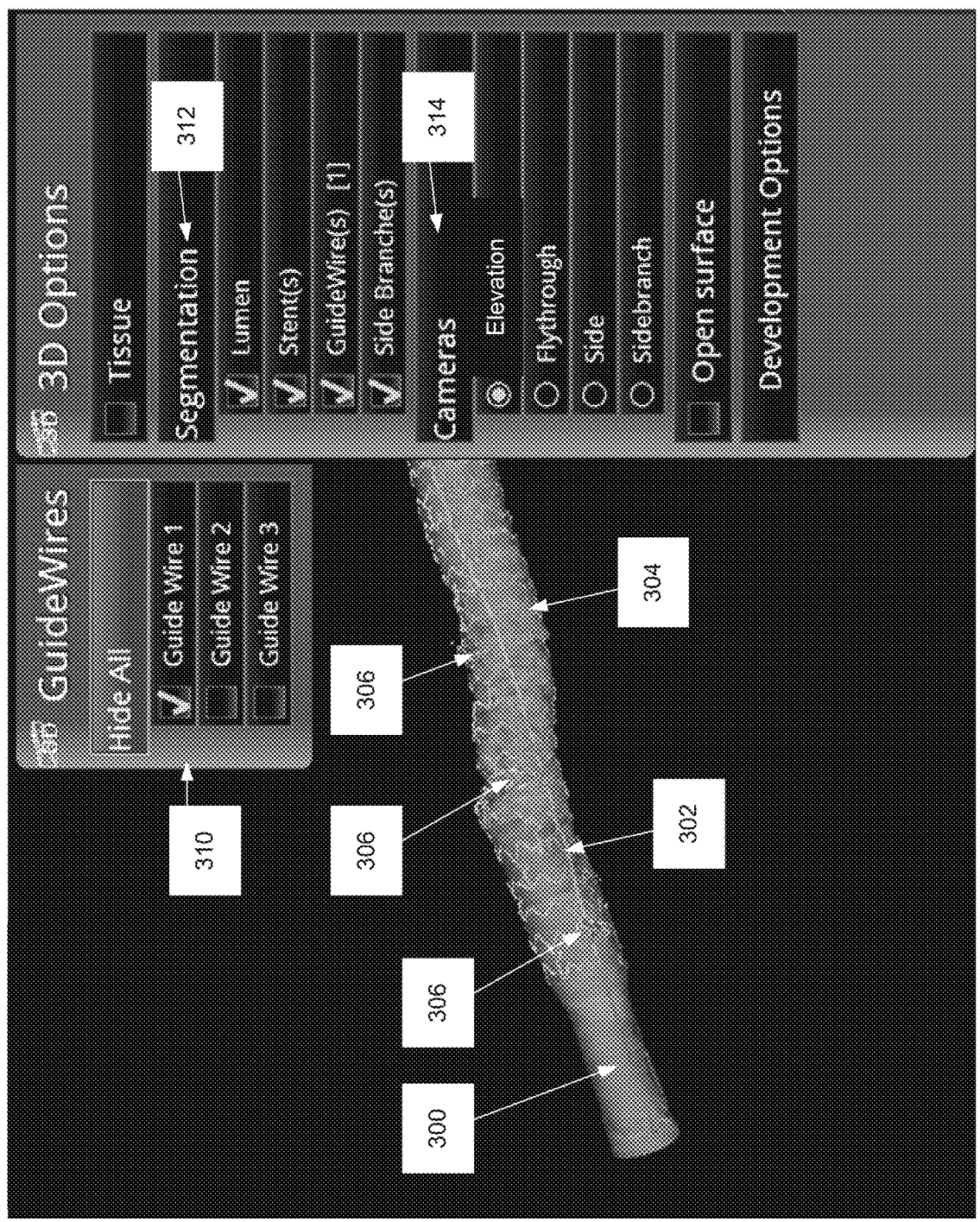
FIG. 8 is a user display showing perspective view of a three-dimensional rendering of a blood vessel according to an illustrative embodiment of the disclosure.

FIG. 8 shows a user display depicting a perspective view of a three-dimensional rendering of a blood vessel 300, in accordance with an embodiment. A guidewire 302, stent struts 304, and indicia demarcating jailed side branches 306 are visible. The user display includes a menu 310 for showing/hiding guidewires, a menu 312 for selecting blood vessel features to display, and a menu 314 for selecting the virtual camera angle of the display. The user can toggle between multiple view angles on the user display. In addition, the user can toggle between different side branches on the user display, such as by selecting particular side branches and/or by selecting a camera associated with a particular side branch.

FIGS. 9A-9C show a user display integrating a side view of a three-dimensional rendering (FIG. 9A), a corresponding B-mode OCT image (FIG. 9B), and a corresponding L-mode OCT image (FIG. 9C). FIG. 9A is a side view of a three-dimensional rendering of a blood vessel 300. A guidewire 302 and stent struts 304 are visible. FIG. 9B shows a cross sectional B-mode OCT image. A guidewire shadow 312 and numerous stent strut shadows 314 are clearly visible. FIG. 9C shows a longitudinal L-mode OCT image. The guidewire shadow 312 and numerous stent strut shadows are clearly visible. Vertical line 316 demarcates the cross-sectional frame shown in FIG. 9B.

FIGS. 10A-10C show a user display integrating a side view of a three-dimensional rendering (FIG. 10A), a corresponding B-mode OCT image (FIG. 1B), and a corresponding L-mode OCT image (FIG. 10C), similar to FIGS. 9A-9C. FIG. 10A includes visible indicia 306 demarcating jailed side branches.

FIGS. 11A-11C show a user display integrating a fly-through rendering (FIG. 11A), a corresponding B-mode OCT image (FIG. 11B), and a corresponding L-mode OCT image (FIG. 10C). In FIG. 11A, the guidewire 302 and stent struts 304 are shown in a space-filling model. A compass 320 indicates proximal and distal directions.

Figures 12A, 12B, 12C:
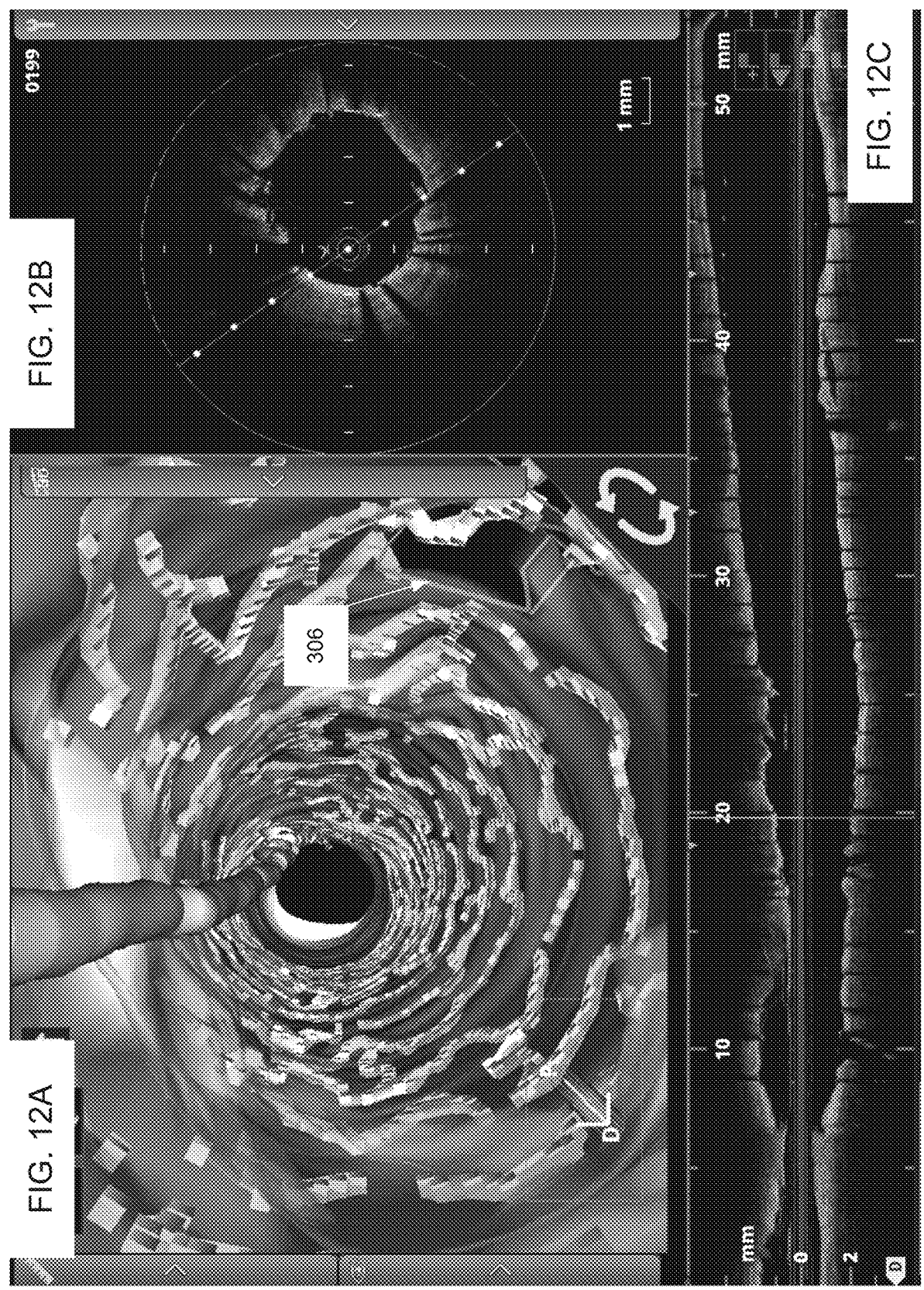
FIG. 12A is a fly-through three-dimensional rendering of a blood vessel showing a jailed side branch according to an illustrative embodiment of the disclosure.
FIG. 12B is a cross-sectional B-mode OCT intravascular image according to an illustrative embodiment of the disclosure.
FIG. 12C is a longitudinal L-mode OCT intravascular image according to an illustrative embodiment of the disclosure.

FIGS. 12A-12C show a similar display as shown in FIGS. 12A-12C. FIG. 12A includes an indicia of a jailed side branch 306, in accordance with an illustrative embodiment.

FIGS. 13A-13C show a user display integrating a side view of a three-dimensional rendering (FIG. 13A), a corresponding B-mode OCT image (FIG. 13B), and a corresponding L-mode OCT image (FIG. 13C), similar to FIGS. 9A-9C. FIG. 13A shows a side branch ostium 322 that was jailed but was deobstructed by cutting the stent strut 324 that had jailed the side branch. FIG. 13D is a zoomed view of FIG. 13A, showing the ostium 322 and cleaved strut 324.

Exemplary Intravascular Data Collection Embodiments

Figure 14A:
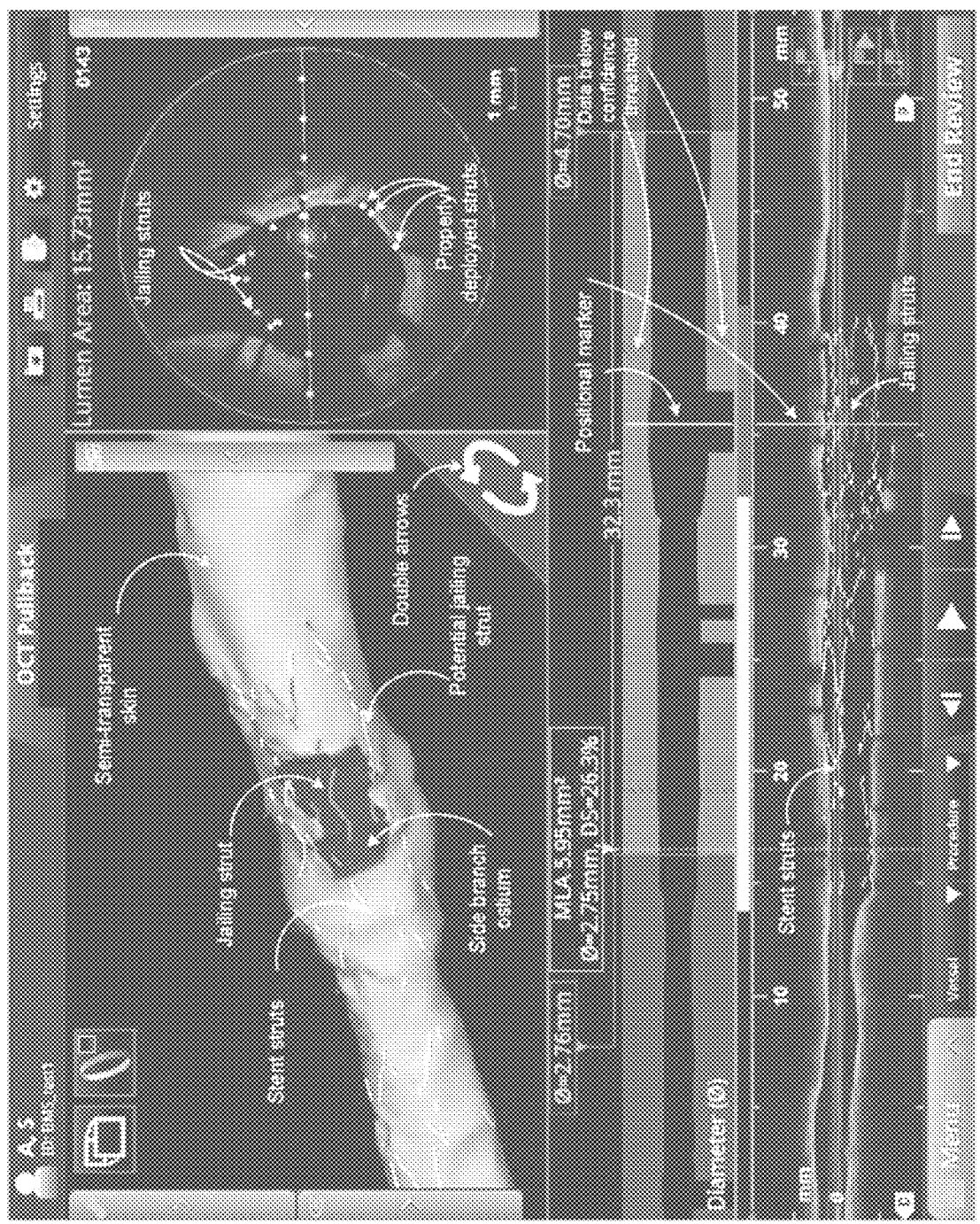
FIGS. 14A, 14B, 14C, 14D show graphic user interface displays of an intravascular data collection system exemplifying a three dimensional skin and wire frame view of a deployed stent according to an illustrative embodiment of the disclosure.

The systems and methods described herein provide diagnostic information to support imaging needs before and after interventions related to specific clinical applications for bifurcation, BVS, VFR for other complex conditions such as tandem lesions/diffuse diseases. The embodiments include features as:

- 3D options for fly-through, longitudinal and branch view
- OCT use and stent detection for BVS procedural considerations
- Ultra-high resolution pull back for bifurcation cases
- Independent wire selection on 3D in addition to multiple 3D display options
- Stent apposition mapping indicator; addition of status bar for 360 degree assessment
- Apposition indicator ranges for Red/yellow and customization ability to adjust ranges
- Various user interface design elements FIG. 14A shows an interface display exemplifying a three dimensional, skin and wire-frame view of a deployed stent based on OCT imaging data. The upper left panel shows an elevation view of a blood vessel and, specifically, the endoluminal boundary of a blood vessel is depicted in three dimensions as a semi-transparent skin. The skin estimates or approximates the topography of the blood vessel wall and/or the blood vessel lumen along a region of interest. In a preferred embodiment, the skin closely approximates the contours of the lumen to enhance user visualization of blood vessel topography, such as side branches, healthy endothelium, stenonses, lesions, and plaques. The skin can be depicted in any suitable color and preferably is semi-transparent to permit visualization of stents deployed within the lumen.

Figure 14B:
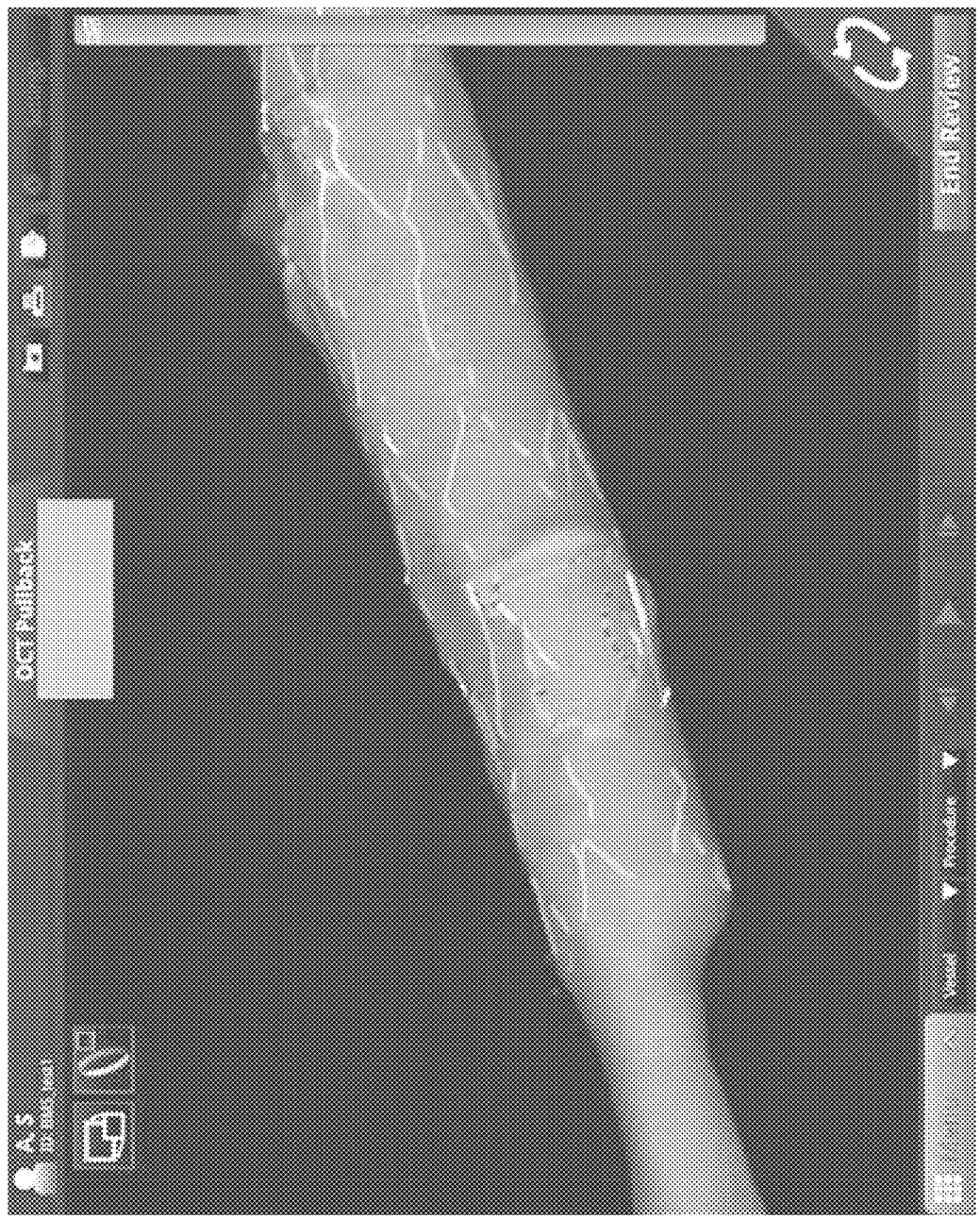

As with other user interfaces, the double arrows allow a user to rotate the skin view. As shown in FIG. 14A, in some embodiments, the skin itself has no thickness (i.e., is two-dimensional) and merely demarcates the endoluminal boundary in three dimensions. In other embodiments the skin can have nominal or substantial thickness to enhance feature visualization. The transparency level of the lumen, skin or other layers can be adjusted to enhance the overlay of features such as stent struts. As shown in FIG. 14B, side branch detection is enhanced using a three-dimensional interface for supporting bifurcation procedures as well as an input to VFR calculations.

Figure 15A:
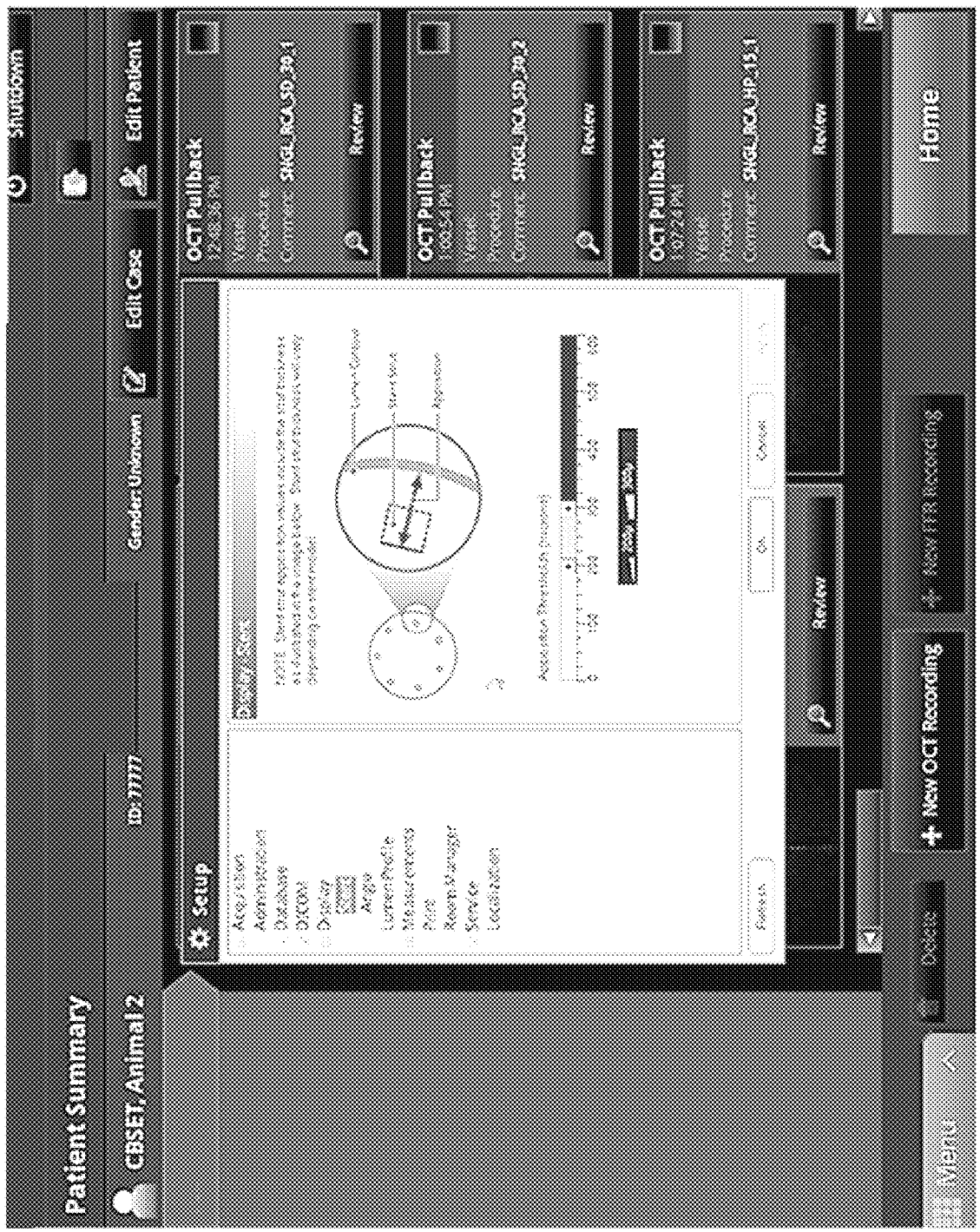
FIGS. 15A, 15B, 15C are user interfaces that include a user input device suitable for adjusting apposition thresholds that in turn control the threshold an intravascular data collection system uses when determining when to display apposition and the indicator/indicia (color, symbol, etc) to use according to an illustrative embodiment of the disclosure.
Figure 15B:
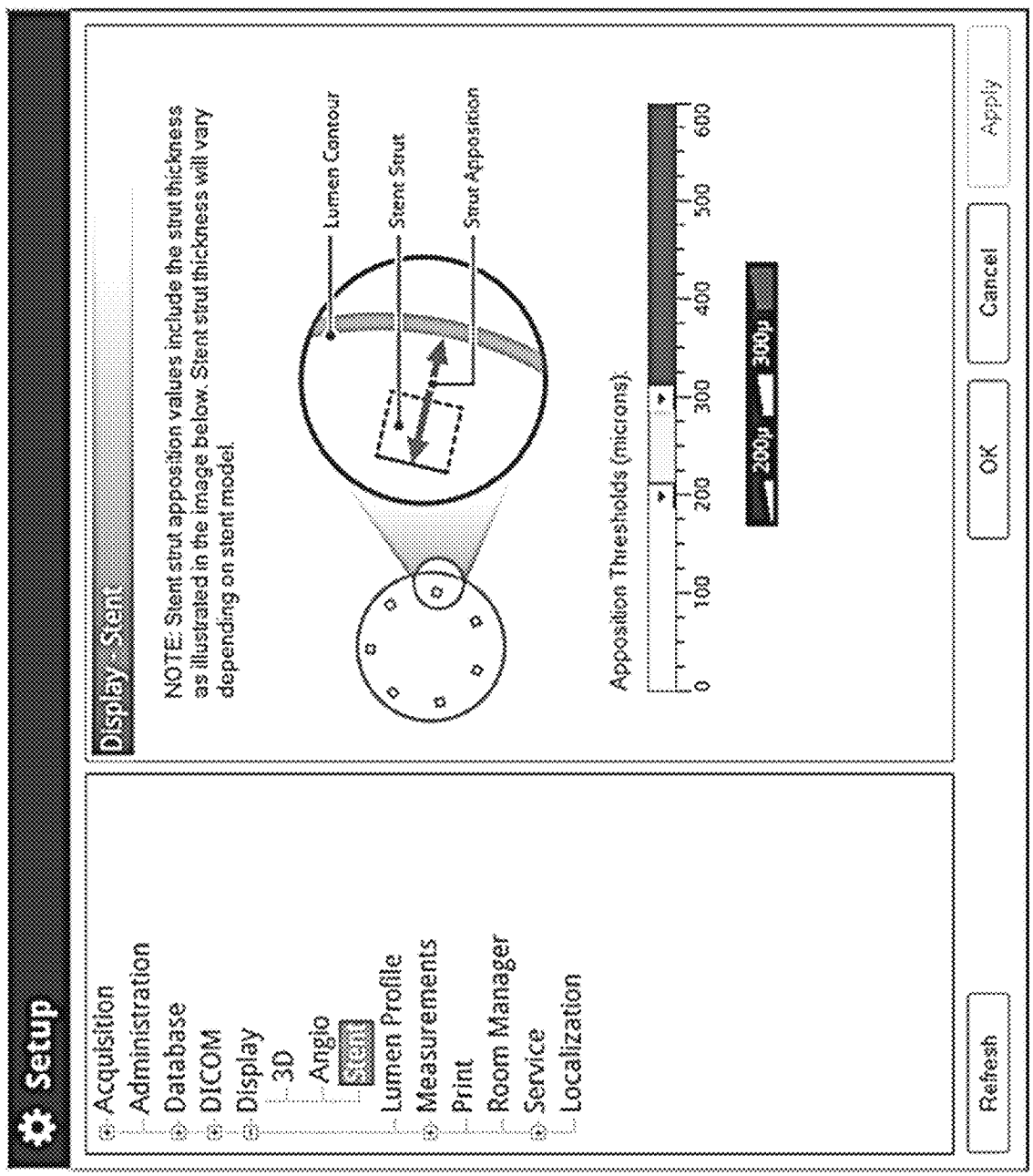
Figure 15C:
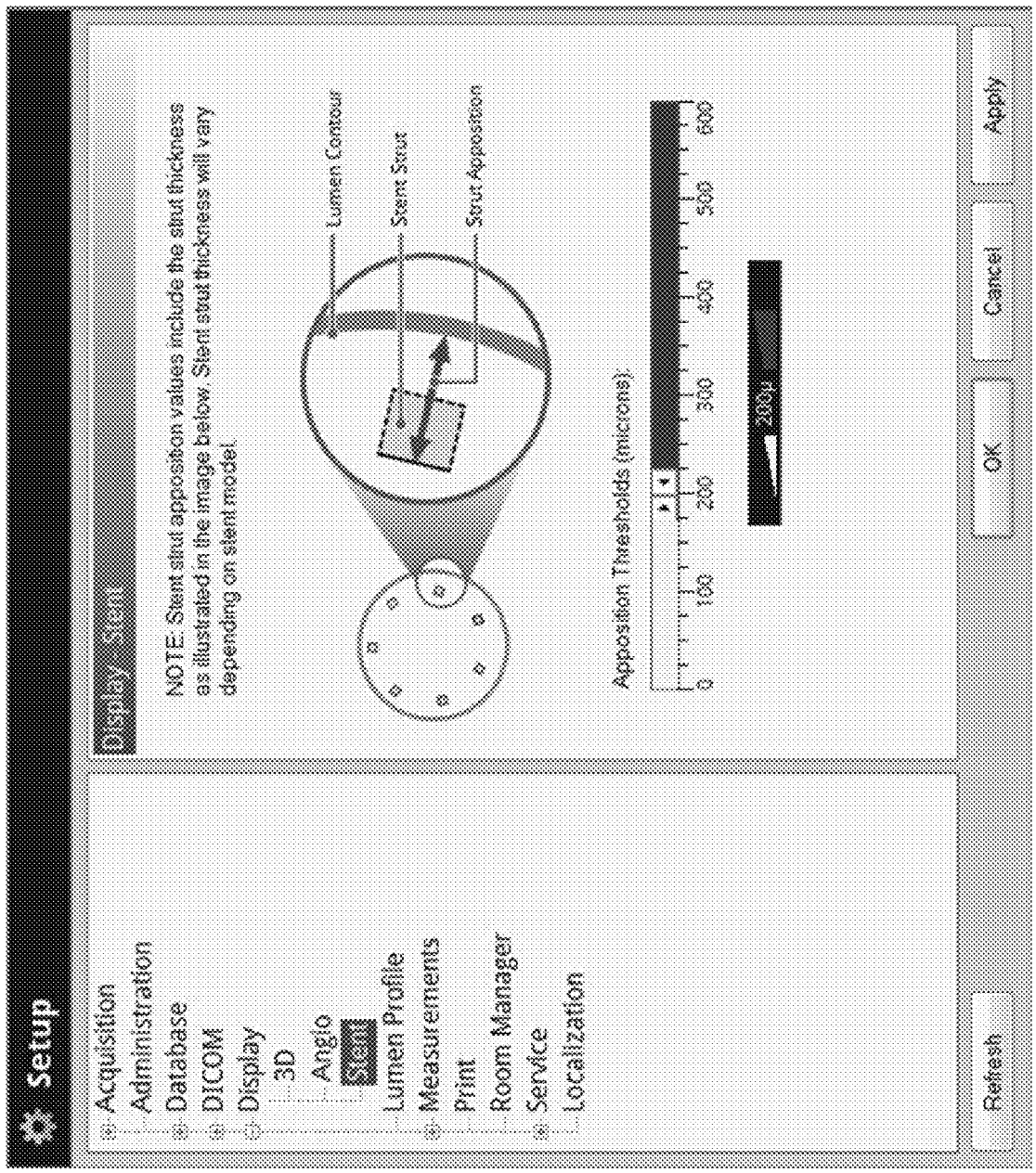

With continued reference to FIG. 14A, the upper left panel depicts a deployed stent as a wire frame graphic behind, or inside, the semi-transparent skin. A side branch ostium is visible as a hole or opening in the skin. Stent struts are visible through the semi-transparent skin. Stent struts can be shown in color, or by other visual indicia, to provide further information about stent deployment and positioning. For example, struts that are properly deployed are shown in one color (e.g., white) and struts that are malapposed (e.g., are under-inflated, jail a side branch, etc.) are shown in a different color (e.g., red). The degree or extent of stent apposition can be conveyed by color gradients, such as white for proper deployment, yellow for potential apposition, and red for likely stent apposition. Different colors also can be used to distinguish between different causes of malapposition and the associated apposition levels or thresholds. These thresholds can be set using a user interface in one embodiment, such as for example as shown in FIGS. 15A-15C. The software and controls for which indicia to display can be implemented using one or more software modules 67.

By way of non-limiting example, stent struts that are properly expanded against the blood vessel wall are shown in one color (e.g., white), whereas under-inflated struts are shown in another color (e.g., purple), to alert the user that further intervention may be required to fully expand the stent at a particular location. Similarly, struts that jail or occlude a side branch ostium can be shown in another color (e.g., red), and potentially jailing struts can be shown in a yet another color (e.g., yellow), to alert a user that stent adjustment or repositioning may be required. As will be appreciated, other visual indicia can be used such as, for example, patterned lines, hatching, and shading.

The top right panel of FIG. 14A shows a cross-section of an OCT image. Stent strut cross-sections are depicted as circles. Stent struts can be shown in color, or by other visible indicia, to convey information to a user about strut positioning. For example, stent struts that are properly expanded against the blood vessel wall are shown in one color (e.g., white), whereas struts that jail the side branch are shown in another color (e.g., red).

The center panel of FIG. 14A shows a longitudinal or L-mode rendering of the OCT data. The cross-section frame corresponds to the vertical line within the region of interest. The bottom panel of FIG. 14A shows an OCT L-mode image of a blood vessel co-registered with a wire-frame representation of a deployed stent. Again, stent struts that are properly expanded against the blood vessel wall are shown in one color (e.g., white), whereas struts that jail the side branch are shown in another color (e.g., red).

Figure 14C:
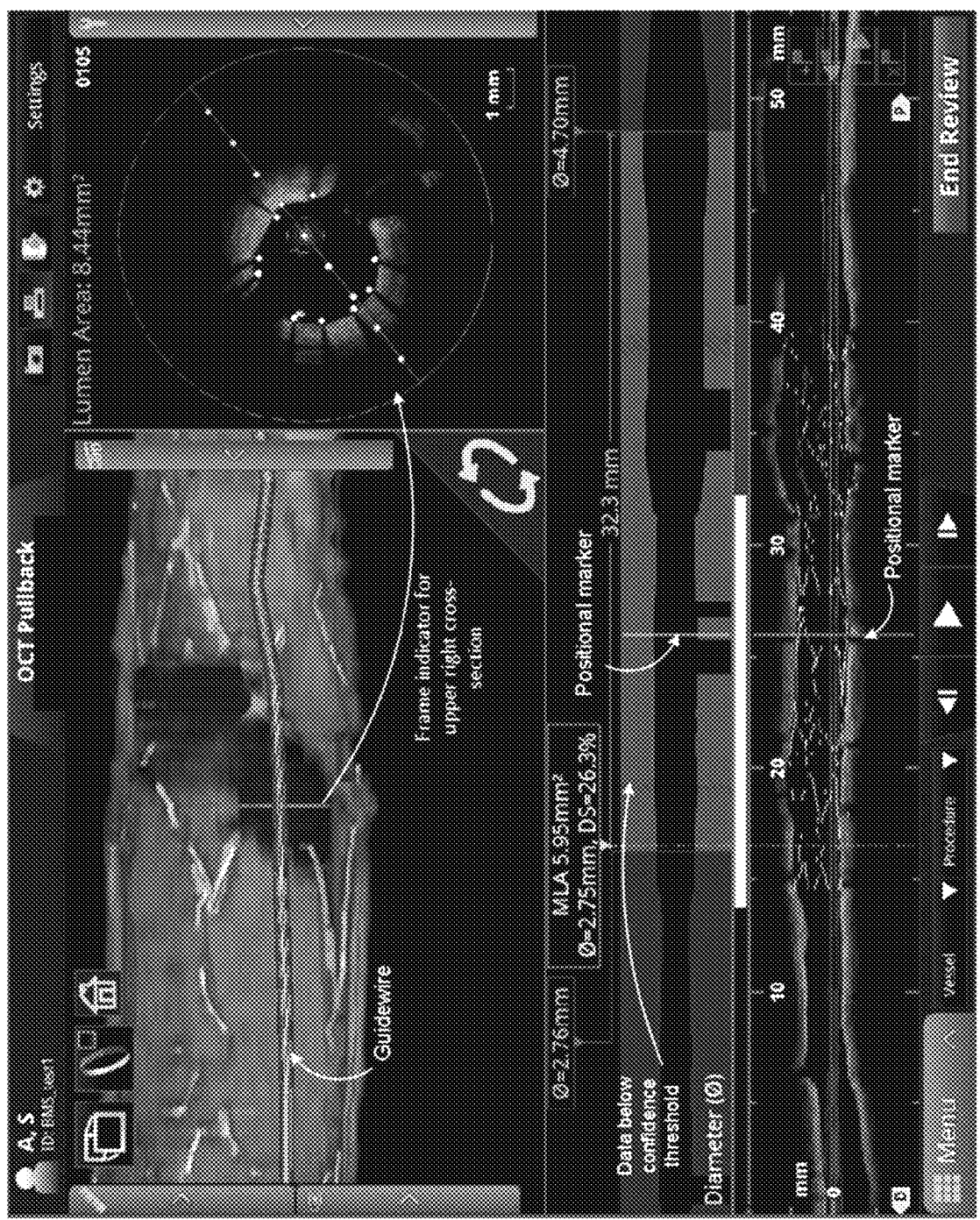

FIG. 14C shows an interface display exemplifying a three dimensional, skin and wire-frame view of a deployed stent based on OCT imaging data. The user display can include the option to display or hide one or more features, such as the skin, guidewire, and/or stent struts. In addition the color and transparency of the skin can be altered, to make the skin more transparent or more opaque.

Figure 14D:
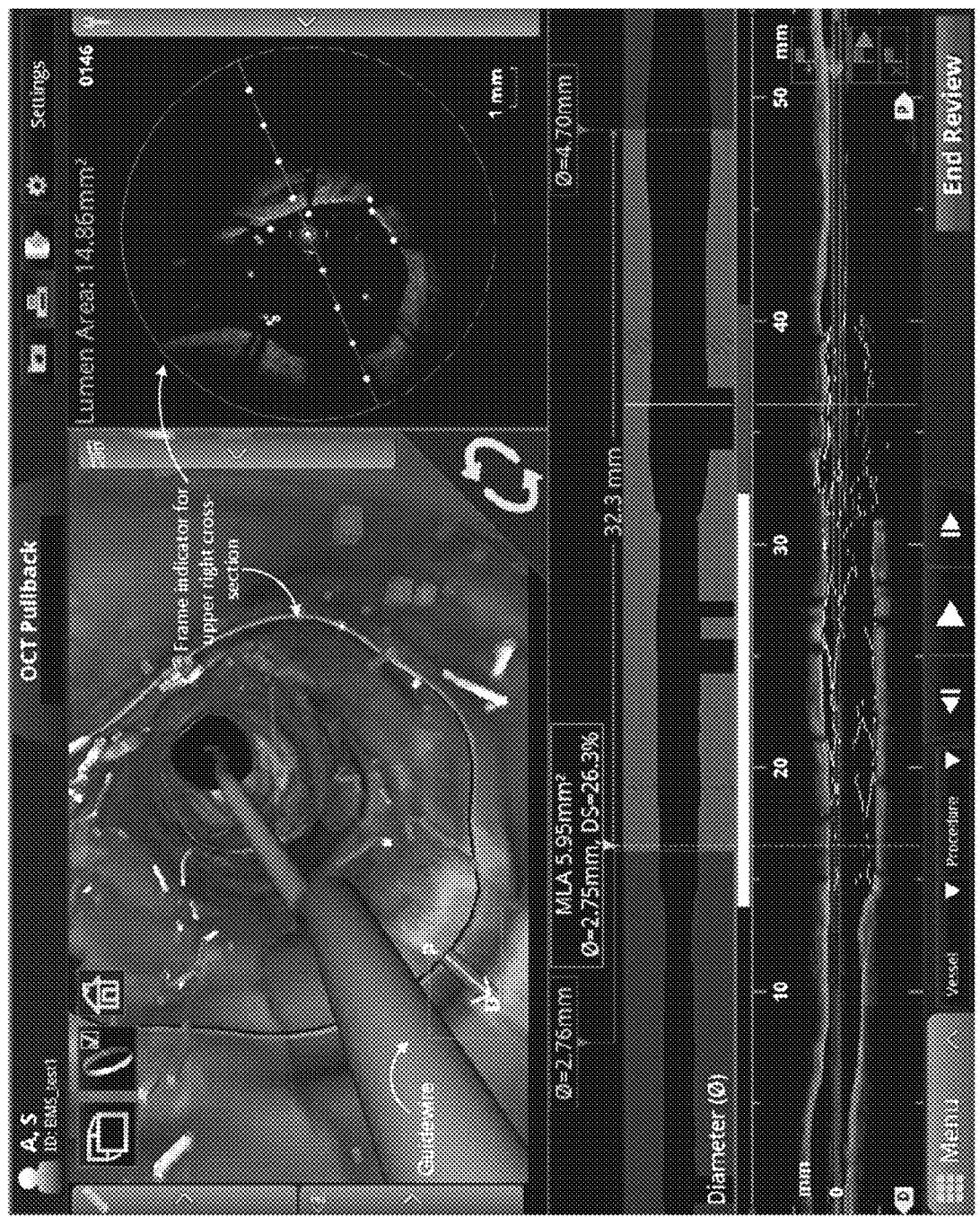

FIG. 14D shows a fly-though display exemplifying a three dimensional, skin and wire-frame view of a deployed stent. Distal (D), or downstream direction and proximal (P), or upstream directions are shown. The interface display also can include a positional marker indicating the location of the cross-sectional images within the region of interest. The interface display can further include a luminal marker that highlights the lumen boundary/contour to make vessel's topography more apparent.

Figure 14E:
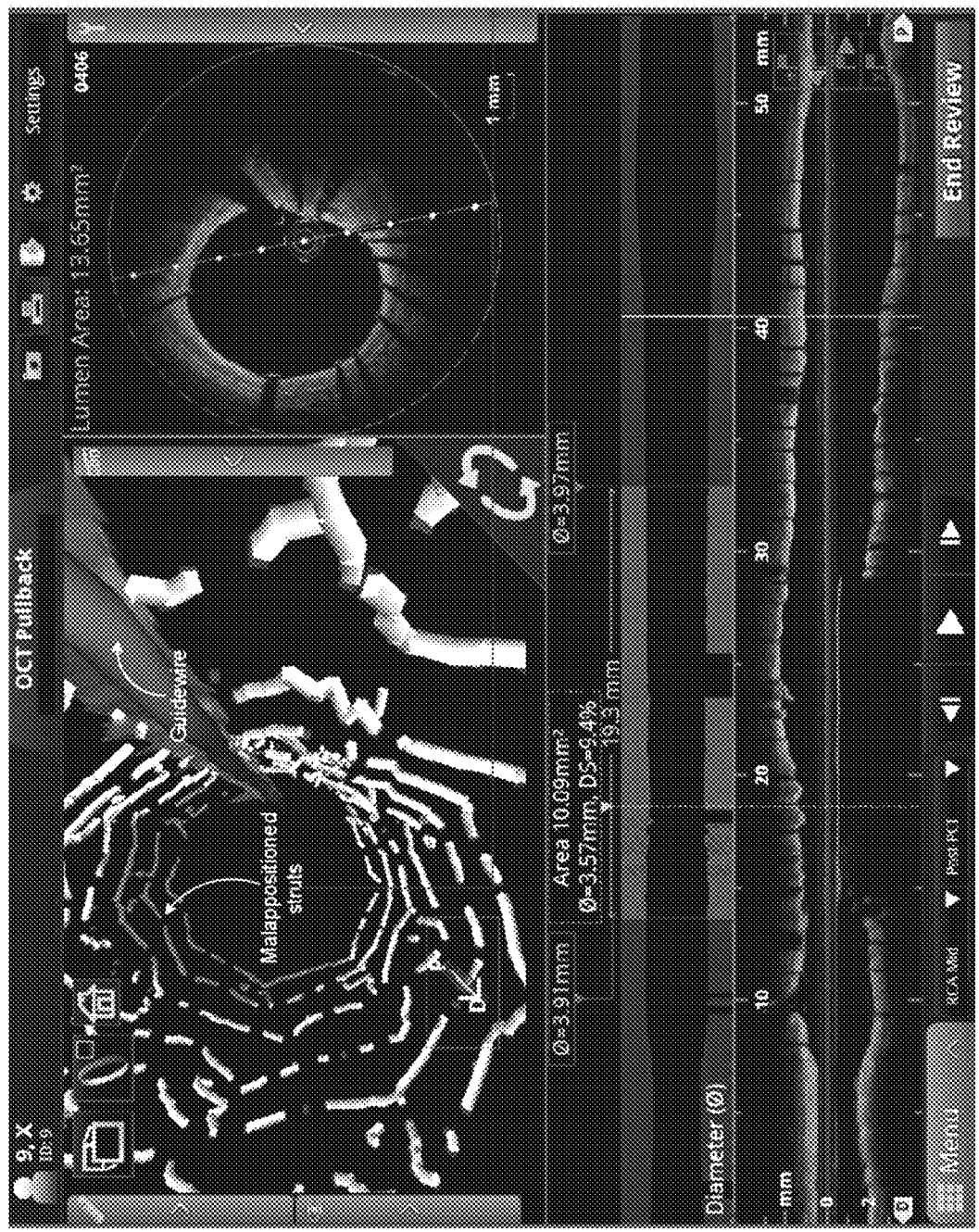
FIG. 14E shows a three dimensional fly-through display of a wire frame view of a deployed stent according to an illustrative embodiment of the disclosure.

FIG. 14E shows a fly-though display exemplifying a three dimensional wire-frame view of a deployed stent. In this embodiment, the skin is not shown, leaving only the stent struts and guidewire. In some situations, stent apposition may be clearer when the skin is not shown. The skin can be toggled on and off as part of the three-dimensional view and three-dimensional fly through relative to the lumen along the length of blood vessel.

User Interface Features for Apposition Levels

The process of establishing stent apposition values such as an apposition threshold can vary from one end user of an intravascular diagnostic system to another. An end user can adjust the apposition thresholds for the stents using an interface as shown in FIGS. 15A, 15B, and 15C. In FIG. 15A, the user interface for adjusting stent apposition values is shown relative to a graphic user interface for an OCT system. This interface can be used for IVUS and other imaging modalities. The stent strut shown by the dotted back has an arrow that can extend to one or more surfaces or within the stent strut as a changed able feature. This allows apposition to be specified relative to a location on or within the strut as of interest to the user. In FIGS. 15A and 15B, the three levels or thresholds for scoring or identify apposition levels are between 0 and 200 microns, 200 and 300 microns, and from 300 microns to 600. As shown in FIG. 15B, the three colored bars shown allow three apposition thresholds to be set. These thresholds control how and when stent apposition is displayed. The strut apposition distance is shown by the double-headed arrow in the figure relative to the stent strut and the lumen contour.

The lumen contour is the detected or calculated boundary of the lumen of the blood vessel. Preferably, the stent strut would be close to the lumen contour. To the extent the strut apposition indicates that the front face of the strut is a known distance from the lumen contour, the end user can use their knowledge of stent thicknesses to set an apposition threshold that meets their individual needs. The apposition threshold can be set as in FIG. 15C such that only two levels appear—apposed or not apposed. Two, three or more such levels can be set. In one embodiment, as shown in FIGS. 15A and 15B the slider bar has been adjusted to set the apposition (malapposition) thresholds such that three indicators are used to modify the graphics of the stent struts displayed. The term apposition can include malapposition as it is used to describe a degree of a stent deviating from its preferred level of expansion or placement relative to a vessel wall.

Levels of stent malapposition, such as by an apposition threshold for evaluating detected stent struts relative to a detected lumen contour, can be defined using a user interface. The interface can be a slider (shown in FIGS. 15A-15C) or other user interfaces such as a toggle control, one or more buttons, a field for percentage or distance or entry of another apposition parameter, or other interfaces to specify how indicia are displayed relative to detected stent struts and the stent strut apposition level. Any suitable interface for selecting or inputting an apposition threshold can be used. In one embodiment, the apposition does not specify stent strut thickness but rather uses the stent strut end face. In this way, the end user can adjust the threshold based on their expertise and the thickness of the stent struts in use.

Non-Limiting Software Features and Embodiments for Implementing Interface, Detection and Other Features of Disclosure The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like. The disclosure can also be practiced in distributed computing environments where tasks are performed by remote processing devices that are linked through a communications network such as in different rooms of a catheter or cath lab.

Some portions of the detailed description are presented in terms of methods such as algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "searching" or "indicating" or "detecting" or "measuring" or "calculating" or "comparing" or "generating" or "sensing" or "determining" or "displaying," or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present disclosure, in some embodiments, also relates to apparatus for performing the operations herein. This apparatus may be specially constructed for the required purposes, or it may comprise a general purpose computer selectively activated or reconfigured by a computer program stored in the computer. Various circuits and components thereof can be used to perform some of the data collection and transformation and processing described herein.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description provided herein. In addition, the present disclosure is not described with reference to any particular programming language, and various embodiments may thus be implemented using a variety of programming languages. In one embodiment, the software instructions are configured for operation on a microprocessor or ASIC of an intravascular imaging/data collection system.

Embodiments of the disclosure may be implemented in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof.

In a typical embodiment of the present disclosure, some or all of the processing of the data collected using an OCT probe, an IVUS probe, other imaging probes, an angiography system, and other imaging and subject monitoring devices and the processor-based system is implemented as a set of computer program instructions that is converted into a computer executable form, stored as such in a computer readable medium, and executed by a microprocessor under the control of an operating system. Thus, user interface instructions and triggers based upon the completion of a pullback or a co-registration request, for example, are transformed into processor understandable instructions suitable for generating OCT data, performing image procession using various and other features and embodiments described above.

In addition, user interface commands, a user query, a system response, transmitted probe data, input data and other data and signal described herein are transformed into processor understandable instructions suitable for responding to user interface selections, controlling a graphical user interface, control and graphic signal processing, displaying cross-sectional information, rendered stents and guidewires and images from other data collection modalities, generating and displaying stents and indicators and other intravascular data, displaying OCT, angiography, detecting shadows, detecting peaks, and other data as part of a graphic user interface and other features and embodiments as described above. Data and parameters suitable for display as GUI components or controls, values, or as another representation in a graphical user interface can include without limitation guidewire, apposition bars, user interface panels, masks, stent struts, missing data representations, shadows, angiography representations, three and two dimensional renders and views, and other features as described herein.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Various examples of suitable processing modules are discussed below in more detail. As used herein a module refers to software, hardware, or firmware suitable for performing a specific data processing or data transmission task. In one embodiment, a module refers to a software routine, program, or other memory resident application suitable for receiving, transforming, routing and processing instructions, or various types of data such as angiography data, OCT data, IVUS data, offsets, shadows, pixels, intensity patterns, guidewire segments, sidebranch orientation, stent orientation, stent position relative to side branch position, user interface data, control signals, angiography data, user actions, frequencies, interferometer signal data, detected stents, candidate stent struts, IVUS data, shadows, pixels, intensity patterns, scores, projections, and guidewire data and other information of interest as described herein.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

The term "machine-readable medium" or "computer-readable-medium" includes any medium that is capable of storing, encoding or carrying a set of instructions for execution by the machine and that cause the machine to perform any one or more of the methodologies of the present disclosure. While the machine-readable medium is shown in an example embodiment to be a single medium, the term "machine-readable medium" should be taken to include a single medium or multiple media (e.g., a database, one or more centralized or distributed databases and/or associated caches and servers) that store the one or more sets of instructions.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously. The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

Furthermore, whereas particular embodiments of the disclosure have been described herein for the purpose of illustrating the disclosure and not for the purpose of limiting the same, it will be appreciated by those of ordinary skill in the art that numerous variations of the details, materials and arrangement of elements, steps, structures, and/or parts may be made within the principle and scope of the disclosure without departing from the disclosure as described in the claims.

Furthermore, whereas particular embodiments of the disclosure have been described herein for the purpose of illustrating the disclosure and not for the purpose of limiting the same, it will be appreciated by those of ordinary skill in the art that numerous variations of the details, materials and arrangement of elements, steps, structures, and/or parts may be made within the principle and scope of the disclosure without departing from the disclosure as described in the claims.

What is claimed is:

1. A processor-based system for controlling stent apposition thresholds based on user inputs, the system comprising:
   one or more memory devices; and
   a computing device in communication with the one or more memory devices, wherein the one or more memory devices comprise instructions executable by the computing device to cause the computing device to:
   display a user interface comprising a stent strut apposition threshold control, the control comprising a user selectable input;
   store a user input stent strut apposition threshold in the one or more memory devices;
   detect one or more stent struts in an intravascular data set, the intravascular data set collected using an intravascular probe;
   cause the computing device to display the one or more stent struts and one or more indicia associated with the one or more stent struts, wherein the indicia indicates whether the user input stent strut apposition threshold has been reached.

2. The system of claim 1 wherein the stent strut apposition threshold control is a slider.

3. The system of claim 1 wherein the user selectable input is one or more values of the slider.

4. The system of claim 1 wherein the indicia is one or more colors.

5. The system of claim 2 wherein the slider is configured to define three apposition thresholds.

6. The system of claim 1 wherein the stent strut apposition threshold control measures stent strut apposition relative to a front face of a stent strut.

7. The system of claim 1 wherein the stent strut apposition threshold control is selected from the group consisting of a form fillable field; a button; a toggle control; a dial, and a numerical selection input.

8. The system of claim 1 wherein the indicia comprises a modification of the appearance of the one or more stent struts on the display.

9. The system of claim 1 wherein the one or more stent struts include a plurality of stent struts, and wherein the stent strut apposition threshold is applied to each of the plurality of stent struts.

10. The system of claim 1 wherein the one or more stent struts include a plurality of stent struts, and wherein the indicia is applied to a subset of the plurality of stent struts.

11. The system of claim 1 wherein the user input stent strut apposition threshold represents a distance that is greater than zero.

\* \* \* \* \*